(12) United States Patent
Rahme et al.

(10) Patent No.: US 8,877,940 B2
(45) Date of Patent: Nov. 4, 2014

(54) ANTIBIOTIC TOLERANCE INHIBITORS

(75) Inventors: Laurence Rahme, Brookline, MA (US); Francois Lepine, Lavaltrie (CA); Melissa Starkey, Philadelphia, PA (US); Biliana Lesic-Arsic, Paris (FR)

(73) Assignees: Institut National de la Recherche Scientifique, Quebec (CA); The General Hospital Corporation, Boston, MA (US)

( * ) Notice: Subject to any disclaimer, the term of this patent is extended or adjusted under 35 U.S.C. 154(b) by 0 days.

(21) Appl. No.: 14/000,600

(22) PCT Filed: Feb. 22, 2012

(86) PCT No.: PCT/US2012/026028
§ 371 (c)(1),
(2), (4) Date: Aug. 20, 2013

(87) PCT Pub. No.: WO2012/116010
PCT Pub. Date: Aug. 30, 2012

(65) Prior Publication Data
US 2014/0066454 A1 Mar. 6, 2014

Related U.S. Application Data

(60) Provisional application No. 61/445,448, filed on Feb. 22, 2011.

(51) Int. Cl.
| | | |
|---|---|---|
| C07D 235/28 | (2006.01) | |
| C07D 263/58 | (2006.01) | |
| A61K 31/4184 | (2006.01) | |
| A61K 31/496 | (2006.01) | |
| C07D 405/12 | (2006.01) | |

(52) U.S. Cl.
CPC ............ *C07D 235/28* (2013.01); *C07D 263/58* (2013.01); *A61K 31/4184* (2013.01); *A61K 31/496* (2013.01); *C07D 405/12* (2013.01)
USPC ....................................... 548/307.1; 514/387

(58) Field of Classification Search
CPC .................................................. C07D 235/28
USPC ...................................................... 548/307.1
See application file for complete search history.

(56) References Cited

U.S. PATENT DOCUMENTS

2007/0292851 A1  12/2007  Rahme et al.
2009/0247506 A1  10/2009  Andersen et al.

FOREIGN PATENT DOCUMENTS

| JP | 2001/048867 A | * | 2/2001 |
| WO | 2010/003533 | | 1/2010 |
| WO | 2010-042225 | | 4/2010 |

OTHER PUBLICATIONS

An English translation of JP 2001/048867, 2001.*
Chemical Abstracts Registry No. 902381-83-3, entered into the Registry file on STN Aug. 17, 2006.*
International Search Report and Written Opinion mailed Aug. 22, 2012 in International Application No. PCT/US2012/026028, 13 pgs.
PubChemCompound, datasheet [online compound summary] Retrieved from the Internet: <IIRL: http://pubchem,ncbi,nlra,nih,gov/search/search,cgi> See CID 1315490, CID 1291814, CID 4149071, CID 42587908, CID 1232954, CID 7756204, CID 2347323, CID 2335764, CID 2610664, and CID 2120563, Jul. 11, 2005.
Malladi Srinivas Reddy et al., "Synthesis, characterization and biological evaluation of some novel 2-substitued mercaptobenzimidazole derivatives". Pharmaceutical Chemistry Journal, 44(11): 642-645 (Feb. 2011) (Russian original vol. 44, No. 11, Nov. 2010), IS.SN 0091-150.X.
Liliva N, Kirpotina et al., "Identification of Novel .Small-Molecule Agonists for Human Forrayl Peptide Receptors and Pharmacophore Models of Their Recognition", Molecular Pharmacology 77(2): 159-170 (2010).
International Preliminary Report in International Application No. PCT/US2012/026028, issued Aug. 27, 2013, 9 pages.
Apidianakis et al., "Synergy between bacterial infection and genetic predisposition in intestinal dysplasia," PNAS, Dec. 8, 2009, 106(49):20883-20888.
Berge et al., "Pharmaceutical Salts," Journal of Pharmaceutical Science, 1977, 66(1):1-19.
Boucher et al., "Bad bugs, no drugs: no ESKAPE! An update from the Infectious Diseases Society of America," Clin Infect Dis, 2009, 48(1):1-12.
Brett et al., "*Burkholderia thailandensis* sp. nov., a *Burkholderia pseudomallei*-like species," Int J Syst Bacteriol, 1998, 48(1):317-320.
Bures et al., "Small intestinal bacterial overgrowth syndrome," World J Gastroenterol., Jun. 28, 2010, 16(24):2978-2990.
Burli et al., "DNA binding ligands targeting drug-resistant Gram-positive bacteria. Part 1: Internal benzimidazole derivatives," Bioorg. Medicinal Chem. Lett., Mar. 8, 2004, 14(5):1253-1257.
Calfee et al., "Interference with *Pseudomonas quinolone* signal synthesis inhibits virulence factor expression by *Pseudomonas aeruginosa*," Proc Natl Acad Sci U S A, 2001, 98(20):11633-7.
Cao et al., "A quorum sensing-associated virulence gene of *Pseudomonas aeruginosa* encodes a LysR-like transcription regulator with a unique self-regulatory mechanism," Proc Natl Acad SCI USA, 2001, 98(25):14613-14618.
Castang et al., "H-NS family members function coordinately in an opportunistic pathogen," Proc Natl Acad Sci USA, 2008, 105(48):18947-52.
Cegelski et al., "The biology and future prospects of antivirulence therapies," Nat Rev Microbiol, 2008, 6(1):17-27.
Coleman et al., "*Pseudomonas aeruginosa* PqsA is an anthranilate-coenzyme A ligase," J Bacteriol, 2008, 190(4):1247-55.
Cugini et al., "Farnesol, a common sesquiterpene, inhibits PQS production in *Pseudomonas aeruginosa*," Mol Microbiol, 2007, 65(4):896-906.
Dalton et al, "An In Vivo Polymicrobial Biofilm Wound Infection Model to Study Interspecies Interactions," PLoS One, 2011, 6(11):e27317, pp. 1-10.
Déziel et al., "Analysis of *Pseudomonas aeruginosa* 4-hydroxy-2-alkylquinolines (HAQs) reveals a role for 4-hydroxy-2-heptylquinoline in cell-to-cell communication," Proc Natl Acad Sci U S A, 2004, 101(5):1339-1344.

(Continued)

*Primary Examiner* — Laura L. Stockton
(74) *Attorney, Agent, or Firm* — Fish & Richardson P.C.

(57) ABSTRACT

The present disclosure relates to benzimidazole-benzamide derivatives, and the use thereof, e.g., to treat infections.

20 Claims, 27 Drawing Sheets

(56) References Cited

OTHER PUBLICATIONS

Déziel et al., "The contribution of MvfR to *Pseudomonas aeruginosa* pathogenesis and quorum sensing circuitry regulation: multiple quorum sensing-regulated genes are modulated without affecting lasRI, rhlRI or the production of N-acyl-L-homoserine lactones," Mol Microbiol, 2005, 55(4):998-1014.

Diggle et al., "Functional genetic analysis reveals a 2-Alkyl-4-quinolone signaling system in the human pathogen *Burkholderia pseudomallei* and related bacteria," Chem Biol, 2006, 13(7):701-10.

Elnima et al., "Antibacterial and antifungal activities of benzimidazole and benzoxazole derivatives," Antimicrob. Agents Chemother., 1981, 19(2):29-32.

Essar et al., "Identification and characterization of genes for a second anthranilate synthase in *Pseudomonas aeruginosa*: interchangeability of the two anthranilate synthases and evolutionary implications," J Bacteriol, 1990, 172(2):884-900.

Farrow III and Pesci, "Two distinct pathways supply anthranilate as a precursor of the *Pseudomonas* quinolone signal," J Bacteriol, 2007, 189(9):3425-33.

Farrow III, et al., "PqsE Functions Independently of PqsR-*Pseudomonas* Quinolone Signal and Enhances the rhl Quorum-Sensing System," J. Bacteriol., 2008, 190(21):7043-7051.

Gallagher et al., "Functions required for extracellular quinolone signaling by *Pseudomonas aeruginosa*," J Bacteriol, 2002, 184(23):6472-80.

Hazan et al., "Homeostatic Interplay between Bacterial Cell-Cell Signaling and Iron in Virulence," PLoS Pathog, 2010, 6(3):e1000810, pp. 1-14.

Iwahi et al., "Lansoprazole, a novel benzimidazole proton pump inhibitor, and its related compounds have selective activity against *Helicobacter pylori*," Antimicrob. Agents Chemother., Mar. 1991, 35(3):490-496.

Kedderis and Miwa, "The metabolic activation of nitroheterocyclic therapeutic agents," Drug Metab Rev, 1988, 19(1):33-62.

Kesarwani et al., "A Quorum Sensing Regulated Small Volatile Molecule Reduces Acute Virulence and Promotes Chronic Infection Phenotypes," PLoS Pathog. Aug. 7, 2011(8):e1002192, pp. 1-12.

Koo and DuPont, "Rifaximin: a unique gastrointestinal-selective antibiotic for enteric diseases," Current Opin Gastroenterol., 2010, 26:17-25.

Lepine et al., "A stable isotope dilution assay for the quantification of the *Pseudomonas* quinolone signal in *Pseudomonas aeruginosa* cultures," Biochim Biophys Acta, 2003, 1622(1):36-41.

Lepine et al., "PqsA is required for the biosynthesis of 2,4-dihydroxyquinoline (DHQ), a newly identified metabolite produced by *Pseudomonas aeruginosa* and *Burkholderia thailandensis*," Biol Chem, 2007, 388(8):839-45.

Lesic et al, "Inhibitors of pathogen intercellular signals as selective anti-infective compounds," PLoS Pathog, 2007, 3(9):1229-39.

Li et al., "The Multifaceted Proteins MvaT and MvaU, Members of the H-NS. Family, Control Arginine Metabolism, Pyocyanin Synthesis, and Prophage Activation in *Pseudomonas aeruginosa* PAO1," J. Bacteriol., 2009, 191(20):6211-6218.

McManus et al. "Antibiotic Use in Plant Agriculture" Annu. Rev. Phytopathol., 2002, 40:443-65.

Mosmann, "Rapid colorimetric assay for cellular growth and survival: application to proliferation and cytotoxicity assays," J Immunol Methods, 1983, 65(1-2):55-63.

Muh et al., "Novel *Pseudomonas aeruginosa* quorum-sensing inhibitors identified in an ultra-high-throughput screen," Antimicrob Agents Chemother, 2006, 50(11):3674-9.

Persson et al., "Quorum sensing inhibition: targeting chemical communication in gram-negative bacteria," Curr Med Chem, 2005, 12(26):3103-15.

Pustelny et al., "Dioxygenase-mediated quenching of quinolone-dependent quorum sensing in *Pseudomonas aeruginosa*," Chem Biol, 2009, 16(12):1259-67.

Rahme et al., "Common virulence factors for bacterial pathogenicity in plants and animals," Science, 1995, 268(5219):1899-902.

Rezaie et al., "Common pathogens in burn wound and changes in their drug sensitivity," Burns, 2011, 37(5):805-7.

Schweizer, "Allelic exchange in *Pseudomonas aeruginosa* using novel ColE1-type vectors and a family of cassettes containing a portable oriT and the counter-selectable *Bacillus subtilis* sacB marker," Molecular Microbiology, 1992, 6(9):1195-1204.

Smith and Iglewski, "*P. aeruginosa* quorum-sensing systems and virulence," Current Opinion in Microbiology, 2003, 6(1):56-60.

Stevens et al., "A quantitative model of invasive *Pseudomonas* infection in burn injury," J Burn Care Rehabil., 1994, 15:232-235.

Tashiro et al., "Bicyclic compounds repress membrane vesicle production and *Pseudomonas* quinolone signal synthesis in *Pseudomonas aeruginosa*," FEMS Microbiology Lett., 2010, 304(2):123-130.

Vial et al., "*Burkholderia pseudomallei, B. thailandensis*, and *B. ambifaria* produce 4-hydroxy-2-alkylquinoline analogues with a methyl group at the 3 position that is required for quorum-sensing regulation," J Bacteriol, 2008, 190(15):5339-52.

Xiao et al., "Mutation analysis of the *Pseudomonas aeruginosa* mvfR and pqsABCDE gene promoters demonstrates complex quorum-sensing circuitry," Microbiology, 2006, 152(Pt 6):1679-86.

Xiao et al., "MvfR, a key *Pseudomonas aeruginosa* pathogenicity LTTR-class regulatory protein, has dual ligands," Mol Microbiol, 2006, 62(6):1689-99.

Yang et al., "Effects of iron on DNA release and biofilm development by *Pseudomonas aeruginosa*," Microbiology, 2007, 153(Pt 5):1318-28.

Zhang et al., "A Simple Statistical Parameter for Use in Evaluation and Validation of High Throughput Screening Assays," J Biomol Screen, 1999, 4(2):67-73.

Zhang et al., "PqsD is responsible for the synthesis of 2,4-dihydroxyquinoline, an extracellular metabolite produced by *Pseudomonas aeruginosa*," J Biol Chem, 2008, 283(43):28788-94.

Extended European Search Report issued in EP12749134.8 on Jun. 30, 2014 (9 pages).

Kaplancikli, Zafer, "Synthesis of some novel Carbazole derivatives and evaluation of their antimicrobial activity," Marmara Pharmaceutical Journal, 3(15):105-109 (2011).

Accession No. CID 2347323, Database Pubchem [Online] National Center for Biotechnology Information (Jul. 15, 2005).

El-Sherief et al., "Synthesis of Some New Benzoxazole, Benzthiazole and Benzimidazole Derivatives with Biological Activity," Journal of the Indian Chemical Society, 60(1);58-60 (1983).

\* cited by examiner

| Structure | Lab ID | residual concentration | | | | | | residual | | | | | | |
|---|---|---|---|---|---|---|---|---|---|---|---|---|---|---|
| | | HHQ | PQS | HQNO | 2-AA | DHQ | AA | Data | pyocyanin | score | CAS no | Formula | MW | Reagent Source ID / residual conc. |
| (3-F benzyl bromoketone) | BFPA | 100.00 | 96.00 | 97.00 | 1.23 | | 2.50 | 5 ug/ml (21 uM) | | | 73392-04-8 | C8H7Br1F1N1 O1 | 232.10 | |
| | | 100.00 | 95.00 | 93.00 | 1.10 | 1.32 | 1.79 | 10 ug/ml (42 uM) 10uM | 0.04 0.76 | | | | | |
| | M64 | 0.00 | 0.04 | 0.05 | 0.17 | 0.06 | 12.74 | 100 uM | 0.08 | | | | 420.44 | not |
| | | 0.00 | 0.04 | 0.04 | 0.14 | 0.06 | 14.33 | 10uM | 0.04 | | | | | |
| | | 0.00 | 0.05 | 0.12 | 0.17 | 0.08 | 16.05 | 1uM | 0.04 | | | | | |
| | | 0.45 | 0.36 | 0.37 | 0.48 | 5.77 | 0.31 | 500 nM | | | | | | |
| | | 0.87 | 0.76 | 0.58 | 0.88 | 0.85 | 0.73 | 100 nM | | | | | | |
| | M59 | 0.00 | 0.01 | 0.02 | 0.05 | 0.08 | 5.96 | 100uM | 0.00 | 23.00 | 827001-28-5 | C15 H11 I N4 O3 S | 454.00 | |
| | | 0.00 | 0.01 | 0.03 | 0.04 | 0.05 | 6.07 | 10 uM | 0.00 | 2.10 | | | | |
| | | 0.04 | 0.05 | 0.13 | 0.12 | 0.17 | 5.23 | 1uM | 0.00 | 0.40 | | | | |
| | | 0.13 | 0.36 | 1.56 | 0.08 | 2.29 | 9.90 | 500 nM | 0.02 | | | | | |
| | | 1.12 | 2.67 | 4.99 | 0.43 | 14.04 | 3.45 | 100 nM | 0.19 | | | | | |
| | M50 | 0.04 | 0.05 | 0.06 | 0.04 | 0.04 | 13.27 | 100uM | 0.05 | 22.00 | 381207-51-8 | C15 H11 Br N4 O3 S1 | 407.24 | RyanSci PHAR125935 |
| | | 0.04 | 0.06 | 0.08 | 0.05 | 0.03 | 14.31 | 10 uM | 0.05 | 2.30 | | | | |
| | | 0.20 | 0.21 | 0.35 | 0.18 | 0.19 | 11.27 | 1uM | 0.07 | 0.63 | | | | |
| | M51 | 0.04 | 0.04 | 0.03 | 0.05 | 0.03 | 12.36 | 100uM | 0.05 | 21.00 | 415716-70-0 | C15 H11 Cl N4 O3 S1 | 362.80 | RyanSci PHAR101419 |
| | | 0.04 | 0.05 | 0.07 | 0.06 | 0.04 | 14.19 | 10 uM | 0.05 | 2.30 | | | | |
| | | 0.38 | 0.33 | 0.53 | 0.34 | 0.37 | 9.60 | 1uM | 0.09 | 0.98 | | | | |
| | M62 | 0.02 | 0.07 | 0.12 | 0.10 | 0.08 | 7.99 | 100uM | 0.03 | 31.00 | 866820-77-1 | C16 H11 N5 O3 S | 353.00 | RyanSci PHAR137251 |
| | | | | | | | | 10 uM | 0.04 | 3.10 | | | | |
| | | | | | | | | 1uM | 0.40 | 1.58 | | | | |
| | M24 | 0.03 | 0.10 | 0.17 | 0.12 | | 12.80 | 50 ug/ml (129 uM) | 0.03 | 31.00 | 361178-64-5 | C17H16N4O5S1 | 388.40 | ChemDiv.3448-8855 |
| | | 0.01 | 0.12 | 0.11 | 0.05 | 0.02 | 8.17 | 10uM | 0.04 | 3.10 | | | | |
| | | 0.24 | 1.35 | 0.51 | 0.38 | 0.23 | 8.50 | 5uM | 0.14 | | | | | |
| | | 0.52 | 1.87 | 0.90 | 0.65 | 0.42 | 5.09 | 1uM | 0.15 | | | | | |

FIG. 2A

| | | | | | | | | | | | | | |
|---|---|---|---|---|---|---|---|---|---|---|---|---|---|
| M58 | 0.19 | 0.05 | 0.20 | 0.08 | 0.06 | 12.10 | 100uM | 0.04 | 34.00 | | | | Chembridge |
| | 0.20 | 0.07 | 0.72 | 0.10 | 0.07 | 11.10 | 10 uM | 0.04 | 5.40 | 356775-90-1 | C16 H11 F3 N4 O4 S | 412.00 | 8878559 |
| | 0.43 | 0.70 | 0.88 | 1.10 | 0.93 | 2.97 | 1uM | 0.26 | 2.26 | | | | |
| M27 | | | | | | | 50 ug/ml (132 uM) | 0.05 | 97.00 | 352691-88-4 | C16H14Br1N3 O1S1 | 376.30 | ChemBridge:5 346805 |
| | 0.00 | 0.10 | 0.08 | 0.53 | 0.27 | 15.30 | 10 uM | 0.08 | 6.00 | | | | |
| | 0.01 | 0.07 | 0.07 | 0.30 | 0.27 | 6.17 | 5uM | 0.29 | | | | | |
| | 0.28 | 1.15 | 0.47 | 1.35 | 1.03 | 1.66 | 1uM | 0.52 | | | | | |
| | 0.53 | 1.87 | 0.83 | 1.49 | 1.03 | 0.86 | | | | | | | |
| M61 | 0.02 | 0.08 | 0.13 | 0.11 | 0.10 | 8.28 | 100uM | 0.02 | 32.00 | 381184-64-1 | C16 H14 N4 O4 S | 358.00 | RyanSci PHAR148811 |
| | 0.21 | 0.30 | 0.41 | 0.27 | 0.27 | 5.24 | 10 uM | 0.04 | 8.10 | | | | |
| | 0.82 | 0.76 | 0.74 | 0.89 | 0.95 | 0.67 | 1uM | 0.09 | 3.27 | | | | |
| M52 | 0.04 | 0.05 | 0.04 | 0.12 | 0.18 | 13.19 | 100uM | 0.05 | 33.00 | 41215-95-6 | C15 H12 N4 O3 S1 | 328.40 | RyanSci PHAR151073 |
| | 0.28 | 0.24 | 0.44 | 0.44 | 0.51 | 8.54 | 10 uM | 0.13 | 10.70 | | | | |
| | 0.86 | 0.85 | 0.85 | 1.01 | 0.91 | 0.96 | 1uM | 0.67 | 3.52 | | | | |
| M26 | 0.00 | 0.09 | 0.09 | 0.73 | 0.55 | 4.64 | 50 ug/ml (157 uM) | 0.08 | 155.00 | 41215-89-8 | C15H12Cl1N3 O1S1 | 317.80 | ChemBridge:5 346171 |
| | 0.00 | 0.08 | 0.07 | 0.57 | 0.55 | 4.64 | 10uM | 0.25 | 11.00 | | | | |
| | 0.06 | 0.28 | 0.10 | 1.64 | 1.22 | 1.65 | 5uM | 0.81 | | | | | |
| | 0.11 | 0.56 | 0.18 | 1.75 | 1.29 | 1.21 | 1uM | 0.78 | | | | | |
| M57 | 0.20 | 0.10 | 0.19 | 0.12 | 0.10 | 10.70 | 100uM | 0.04 | 39.00 | 381717-18-6 | C16 H12 N4 O5 S | 372.00 | Chembridge 5349092 |
| | 0.33 | 0.47 | 0.72 | 0.50 | 0.50 | 6.39 | 10 uM | 0.12 | 12.90 | | | | |
| | 0.49 | 0.88 | 0.88 | 1.16 | 1.05 | 1.16 | 1uM | 0.49 | 3.20 | | | | |
| M55 | 0.04 | 0.04 | 0.05 | 0.57 | 0.76 | 8.19 | 100uM | 0.21 | 105.00 | 86109-61-7 | C15 H12 Br O1 S1 | 362.20 | |
| | 0.18 | 0.15 | 0.30 | 0.96 | 1.03 | 4.96 | 10 uM | 0.30 | 17.30 | | | | |
| | 0.87 | 0.85 | 0.88 | 1.26 | 0.91 | 0.93 | 1uM | 0.79 | 3.82 | | | | |
| M23 | 0.00 | 0.09 | 0.11 | 0.88 | 0.83 | 7.14 | 50 ug/ml (153 uM) | 0.25 | 209.60 | 391256-57-8 | C18H19N3O1S 1 | 325.40 | ChemBridge:5 787334 |
| | 0.11 | 0.25 | 0.32 | 0.77 | 0.83 | 3.57 | 10 uM | 0.33 | 14.10 | | | | |
| | 0.62 | 3.17 | 1.63 | 1.89 | 1.22 | 1.00 | 5uM | 0.81 | | | | | |
| | 0.91 | 3.63 | 2.03 | 1.78 | 0.96 | 1.04 | 1uM | 1.00 | | | | | |

FIG. 2B

| Structure | ID | | | | | | | | Conc. | | CAS | Formula | MW | Source |
|---|---|---|---|---|---|---|---|---|---|---|---|---|---|---|
| | B1 | 0.01 | 0.04 | 0.06 | 0.18 | | | | 50 ug/ml (162 uM) | 0.01 | 311314-60-0 | C16H12N4O1S1 | 308.40 | |
| | | 0.93 | 0.55 | 0.59 | 0.74 | | | | 10 ug/ml (32 uM) | 0.12 | | | | |
| | | 1.00 | 0.95 | 0.90 | 1.05 | | | | 2 ug/ml (6 uM) | 0.58 | | | | |
| | | 0.42 | 0.37 | 0.51 | 0.54 | 0.66 | 3.89 | | 10uM | 0.06 | | | | |
| | | 1.13 | 3.75 | 2.26 | 1.34 | 1.13 | 1.12 | 13.60 | 5uM | 0.88 | | | | |
| | | 1.22 | 3.99 | 2.34 | 1.53 | 1.09 | 1.11 | | 1uM | 1.00 | | | | |
| | M53 | 0.23 | 0.28 | 0.42 | 0.23 | 0.29 | 10.98 | | 100uM | 0.07 | 714238-71-8 | C16H14N4O4S1 | 358.40 | RyanSci PHAR094456 |
| | | 0.71 | 0.64 | 0.70 | 0.75 | 0.80 | 4.29 | 77.00 | 10 uM | 0.20 | | | | |
| | | 0.90 | 0.90 | 0.85 | 1.04 | 0.81 | 0.92 | 18.80 | 1uM | 0.66 | | | | |
| | | | | | | | | 3.56 | | | | | | |
| | M18 | 0.05 | 0.08 | 0.16 | 0.00 | | 7.66 | | 50 ug/ml (120 uM) | 0.02 | 878117-60-3 | C25H25N3O3 | 415.50 | Enamine T5531086 |
| | | 0.84 | 0.61 | 0.75 | 0.76 | 0.83 | 2.73 | 32.40 | 10uM | 0.37 | | | | |
| | | | | | | | | 22.20 | | | | | | |
| | M30 | 0.10 | 0.23 | 0.39 | 1.15 | | 4.30 | | 50 ug/ml (128 uM) | 0.25 | 892099-97-7 | C17H12Cl1F1N4O2S1 | 390.80 | ChemDiv E514 0252 |
| | | 0.71 | 0.87 | 0.60 | 0.87 | 0.85 | 1.44 | 247.00 | 10uM | 0.18 | | | | |
| | | | | | | | | 24.70 | | | | | | |
| | M29 | 0.00 | 0.07 | 0.03 | 1.21 | | 2.72 | | 50 ug/ml (93 uM) | 0.55 | 902593-44-6 | C27H25N4O5S1 | 536.50 | ChemDiv C694-0166 |
| | | 0.01 | 0.08 | 0.10 | 1.22 | 1.00 | 1.71 | 202.00 | 10uM | 0.90 | | | | |
| | | | | | | | | 26.80 | | | | | | |
| | M31 | 0.00 | 0.04 | 0.04 | 1.36 | | 5.17 | | 50 ug/ml (116uM) | 0.54 | no CAS | C20H18F1N4O4S1 | 429.40 | ChemDiv C728-0231 |
| | | 0.02 | 0.11 | 0.12 | 1.17 | 0.94 | 1.58 | 247.00 | 10uM | 0.86 | | | | |
| | | | | | | | | 26.60 | | | | | | |
| | M4 | 0.00 | 0.04 | 0.05 | 0.68 | | 4.22 | | 50 ug/ml (151uM) | 0.66 | 361184-66-9 | C16H15N3O1S2 | 329.40 | |
| | | 0.02 | 0.11 | 0.14 | 0.84 | | 2.89 | 246.00 | 10 ug/ml (30uM) | 0.65 | | | | |
| | | 0.03 | 0.10 | 0.16 | 0.65 | | 1.50 | 58.00 | 5ug/ml (15 uM) | | | | | |
| | | 0.03 | 0.14 | 0.20 | 1.22 | 1.03 | 1.45 | | 10uM | 0.71 | | | | |
| | | 0.10 | 1.16 | 0.34 | 2.08 | 1.47 | 1.09 | 26.90 | 5uM | 1.00 | | | | |
| | | 0.14 | 1.76 | 0.55 | 2.01 | 1.46 | 1.10 | | 1uM | 1.00 | | | | |

FIG. 2C

| | | | | |
|---|---|---|---|---|
| M72 | 10uM | | C10H8F3NO | 215.17 | Ambinter T0502-9046 |
| M69 | 10uM | | C20H20ClFN4 | 370.85 | Ambinter STK136799 |
| M71 | 10uM | | C18H22ClN3 | 315.84 | Ambinter STK171407 |
| M70 | 10uM | | C10H11NOS | 193.27 | Ambinter T0514-5256 |
| M67 | 10uM | | C16H11N5O3S2 | 385.42 | Ambinter STOCK5S3S-68293 |
| M66 | 10uM | | C16H13N3O3S | 327.36 | Ambinter BBV-00026165 |

FIG. 2F

| | | | | | | | | | | |
|---|---|---|---|---|---|---|---|---|---|---|
| M39 | 0.35 | 0.28 | 0.47 | 0.36 | 10.37 | | 0.07 | 958086-50-5 | C28H31N5O1 | 453.60 ChemDiv:E009-0106 |
| M43 | 0.34 | 0.35 | 0.36 | 0.26 | 12.70 | 50 ug/ml (110 uM) | 0.03 | 295360-98-4 | C15H13Cl1N2O4 | 320.70 |
| M47 | 0.31 | 0.31 | 0.50 | 0.27 | 0.28 7.83 | 50 ug/ml (156 uM) | 0.09 | 215518-98-2 | C13H9Br1F3N3O1S1 | 392.20 Maybridge:AW00238 |
| M15 | 0.66 | 0.50 | 0.54 | 0.27 | 0.29 5.24 | 50 ug/ml (127 uM) | 0.18 | 8796601-61-3 | C23H24Cl1N3O4 | 441.90 Asinex:ASN13782493 |
| M36 | 0.85 | 0.30 | 0.60 | 0.67 | 5.85 | 50 ug/ml (113 uM) | 0.14 | 364602-28-8 | C22H17N7S1 | 411.50 ChemDiv:5594-8314 |
| M35 | 0.95 | 0.82 | 0.99 | 1.14 | 1.56 | 50 ug/ml (121 uM) | 0.53 | 298687-41-9 | C31H27Cl2N3O4 | 576.50 ChemDiv:8009-1510 |
| M5 | 0.99 | 0.41 | 0.59 | 0.58 | 1.22 | 50 ug/ml (135 uM) strange!! | 0.26 | 919234-31-4 | C19H19N3O3 S | 369.40 |

FIG. 2G

| | | | | | | | | | | | | |
|---|---|---|---|---|---|---|---|---|---|---|---|---|
| M44 | 0.01 | 0.08 | 0.10 | 1.88 | 1.14 | 3.55 | 50 ug/ml (110 uM) | 0.89 | 305.00 | 565192-69-0 | C25H32N4O4 | 452.80 |
| M49 | 0.03 | 0.11 | 0.16 | 0.56 | 1.14 | 1.70 | 50 ug/ml (153 uM) | 0.54 | 323.00 | 311781-19-8 | C18H19N3O1S1 | 325.40 |
| M42 | 0.58 | 0.65 | 0.56 | 0.43 | 0.55 | 6.25 | 50 ug/ml (232 uM) | 0.13 | 322.00 | 64380-24-1 | C10H8F3N1O1 | 215.20 |
| M45 | 0.83 | 0.74 | 0.58 | 0.75 | 0.84 | 1.32 | 50 ug/ml (152 uM) | 0.14 | 357.00 | 41215-93-4 | C15H12N4O3S | 328.30 |
| M38 | 1.00 | 0.77 | 1.00 | 0.82 | | 2.20 | 50 ug/ml (152 uM) | 0.39 | 389.00 | 897766-63-1 | C18H20ClN3O | 329.80 ChemDiv K7835177 |
| M48 | 1.00 | 0.47 | 0.78 | 0.91 | 0.95 | 1.56 | 50 ug/ml (162 uM) | 0.46 | 429.00 | 883224-44-0 | C16H12F3N3O1S1 | 309.00 Maybridge SP 01458 |
| M13 | 1.00 | 0.88 | 0.95 | 0.64 | | 1.87 | 50 ug/ml (201 uM) WT | 0.26 | 470.00 | 5338-99-8 | C14H20N2O2 | 248.30 5535510.00 |

| Company | Plate | Well | Reagent Source | Lab ID | HHQ | PQS | HQNO | 2-AA | AA | Data |
|---|---|---|---|---|---|---|---|---|---|---|
| ChemBridge | 1589 | M02 | 7124491 | M12 | 0 | 86 | 0 | 0.77 | 2.57 | increased HHQ, reduced PQS |
| ChemBridge | 760 | O15 | 5535510 | M13 | 0 | 12 | 5 | 0.64 | 1.87 | WT |
| ChemBridge | 776 | P08 | 5724771 | M14 | | | | | | WT |
| Enamine | 1405 | I06 | T0510-2296 | M16 | 0 | 12.5 | 11 | 0.93 | 0.67 | WT |

FIG. 2L

|  |  | HHQ | PQS | HQNO | 2-AA | DHQ | AA | Data | pyocyanin |
|---|---|---|---|---|---|---|---|---|---|
| M17 | 50 ug/ml | 0.00 | 0.04 | 0.06 | 0.36 |  | 5.99 | 50 ug/ml (176uM) | 0.21 |
|  | 10 uM | 0.51 | 0.52 | 0.67 | 1.07 | 1.16 | 0.84 | 10uM | 0.80 |
| M18 | 50 ug/ml | 0.05 | 0.08 | 0.15 | 0.00 |  | 7.66 | 50 ug/ml (120 uM) | 0.02 |
|  | 10 uM | 0.84 | 0.61 | 0.75 | 0.76 | 0.83 | 2.73 | 10uM | 0.37 |
| M29 | 50 ug/ml | 0.00 | 0.07 | 0.03 | 1.21 |  | 2.72 | 50 ug/ml (93 uM) | 0.55 |
|  | 10 uM | 0.01 | 0.08 | 0.10 | 1.22 | 1.00 | 1.71 | 10uM | 0.90 |
| M31 | 50 ug/ml | 0.00 | 0.04 | 0.04 | 1.36 |  | 5.17 | 50 ug/ml (116uM) | 0.54 |
|  | 10 uM | 0.02 | 0.11 | 0.12 | 1.17 | 0.94 | 1.58 | 10uM | 0.86 |
| M33 | 50 ug/ml | 0.00 | 0.05 | 0.05 | 1.14 |  | 4.95 | 50 ug/ml (134 uM) | 0.30 |
|  | 10 uM | 0.08 | 0.22 | 0.31 | 1.16 | 1.07 | 1.31 | 10uM | 0.74 |
| M8 | 50 ug/ml | 0.00 | 0.05 | 0.05 | 0.53 |  | 3.89 | 50 ug/ml (118 uM) | 0.15 |
|  | 10 uM | 0.05 | 0.20 | 0.25 | 1.24 | 0.96 | 1.39 | 10uM | 0.67 |
| M32 | 50 ug/ml | 0.00 | 0.05 | 0.03 | 1.57 |  | 5.09 | 50 ug/ml (117uM) | 0.96 |
|  | 10 uM | 0.01 | 0.12 | 0.11 | 1.23 | 1.02 | 1.55 | 10uM | 1.16 |
| M41 | 50 ug/ml | 0.00 | 0.05 | 0.10 | 1.38 |  | 4.27 | 50 ug/ml (138 uM) | 0.28 |
|  | 10 uM | 0.43 | 0.55 | 0.67 | 1.21 | 1.01 | 1.02 | 10uM | 0.92 |
| M19 | 50 ug/ml | 0.01 | 0.06 | 0.11 | 0.73 |  | 4.35 | 50 ug/ml (176 uM) | 0.26 |
|  | 10 uM | 0.98 | 0.93 | 0.94 | 1.07 | 0.92 | 0.99 | 10uM | 0.74 |
| M21 | 50 ug/ml | 0.00 | 0.05 | 0.06 | 1.43 |  | 1.46 | 50 ug/ml (153 uM) | 0.95 |
|  | 10 uM | 0.83 | 0.76 | 0.83 | 1.04 | 1.06 | 1.06 | 10uM | 0.88 |

ANTIBIOTIC TOLERANCE INHIBITORS

CLAIM OF PRIORITY

This application is a U.S. National Phase Application under 35 U.S.C. §371 of International Patent Application No. PCT/US2012/026028, filed on Feb. 22, 2012, which claims the benefit of U.S. Provisional Patent Application Ser. No. 61/445,448, filed on Feb. 22, 2011. The entire contents of the foregoing are hereby incorporated by reference.

STATEMENT REGARDING FEDERALLY SPONSORED RESEARCH

This invention was made with Government support under Grant No. AI063433 awarded by the National Institutes of Health. The Government has certain rights in this invention.

TECHNICAL FIELD

The present disclosure relates to benzimidazole-benzamide derivatives, and uses thereof, e.g., in the treatment of acute and chronic infections.

BACKGROUND

Hard-to-eradicate, often untreatable, infections including chronic wounds and infections of medical devices pose increasing threats to human health worldwide. Such infections are often refractory to antibiotics due to antibiotic resistant bacterial cells, and/or to antibiotic tolerance of a sub-population of bacterial cells that are not antibiotic resistant mutants but rather "dormant" cells that survive antibiotic killing. Antibiotic tolerance is defined as the ability of a fraction of a susceptible bacterial population to survive exposure to normally lethal concentrations of bactericidal antibiotics. According to the existing paradigm, many chronic infections are therefore untreatable.

SUMMARY

The present disclosure provides, inter alia, MvfR inhibitors that are compounds of Formula I:

Formula I or pharmaceutically acceptable salts thereof, wherein the constituent variables are defined herein.

The present disclosure further provides pharmaceutical compositions comprising a compound of the disclosure and a pharmaceutically acceptable carrier.

The present disclosure further provides methods of treating an antibiotic-tolerant infection, e.g., a gram-negative infection, e.g., with a compound described herein, e.g., as described below or shown in FIG. 2A-L, 3A-C, or 4, or a pharmaceutically acceptable salt thereof. The methods can also include administering one or more additional antibiotics as known in the art.

The present disclosure further provides methods of treating an infection, e.g., a Gram negative infection, e.g., an acute or chronic infection, with a compound described herein, e.g., as described below or shown in FIG. 2A-L, 3A-C, or 4, or a pharmaceutically acceptable salt thereof. The methods can also include administering one or more additional antibiotics as known in the art.

The present disclosure further provides methods of identifying compounds that inhibit antibiotic-tolerant infections.

In one aspect, the present disclosure features compounds of Formula I:

Formula I or a pharmaceutically acceptable salt thereof, wherein:
Y is $(CH_2)_p$, O, or a bond;
Ring A is aryl, heteroaryl, heterocycloalkyl, substituted by 1 to 5 $R^1$;
$R^1$ is H, —$NR^aR^b$, $NO_2$, or —$NHC(O)R^c$; or 2 $R^1$ together with the carbon atoms to which they are attached form a heteroaryl or heterocycloalkyl;
$R^2$ is H, $C_{1-6}$ alkyl, $C_{1-6}$ alkoxy, —$NR^aR^b$, —$NHC(O)R^a$, $NO_2$, —CN, —$SR^a$, —$S(O)_2R^a$;
$R^a$ and $R^b$ are each independently H or $C_{1-6}$ alkyl;
$R^c$ is H, $C_{1-6}$ alkyl, $C_{1-6}$ haloalkyl;
m is 1, 2, 3, or 4; and
p is 1, 2, 3, 4, 5, or 6.
In some embodiments, Y is O.
In some embodiments, Y is O and Ring A is phenyl substituted by 1 to 5 $R^1$.

In another aspect, the present disclosure features a compound, or a pharmaceutically acceptable salt thereof, having Formula Ia:

Formula I-a

In some embodiments, the compound is:

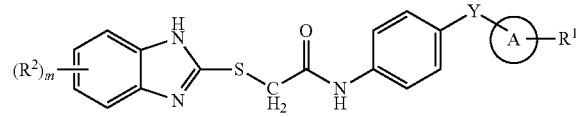

2-((6-nitro-1H-benzo[d]imidazol-2-yl)thio)-N-(4-phenoxyphenyl)acetamide, or a pharmaceutically acceptable salt thereof.

In some embodiments, the compound is:

2-((6-nitro-1H-benzo[d]imidazol-2-yl)thio)-N-(4-phenoxyphenyl)acetamide.

In some embodiments, the present disclosure features a composition comprising a compound of Formula I or I-a, or a pharmaceutically acceptable salt thereof, and a pharmaceutically acceptable carrier. Also provided herein are methods for using these compositions for the treatment of infections, e.g., antibiotic-tolerant infections, in a subject.

In another aspect, the present disclosure features methods of treating an infection, e.g., an antibiotic-tolerant infection in a subject. The methods include administering to the subject a therapeutically effective amount of a compound of Formula I-b:

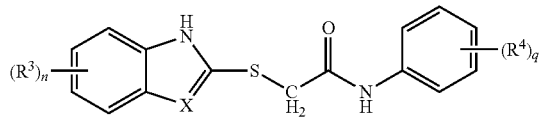

Formula I-b or a pharmaceutically acceptable salt thereof, wherein:
X is O or N;
$R^3$ is H, $C_{1-6}$ alkyl, $C_{1-6}$ alkoxy, —$NO_2$, —$NHC(O)R^c$;
$R^4$ is H, halo, $C_{1-6}$ alkyl, $C_{1-6}$ alkoxy, aryloxy, $C_{1-6}$ haloalkyl, —CN, —$NO_2$, —$SR^a$; or 2 $R^4$ together with the carbon atoms to which they are attached form a heteroaryl or heterocycloalkyl;
$R^a$ is H or $C_{1-6}$ alkyl;
$R^c$ is H, $C_{1-6}$ alkyl, $C_{1-6}$ haloalkyl; and
n and q are each independently 1, 2, 3, 4, or 5.

In some embodiments, the compound is:
2-((1H-benzo[d]imidazol-2-yl)thio)-N-(4-cyanophenyl)acetamide;
2-((1H-benzo[d]imidazol-2-yl)thio)-N-(3-(methylthio)phenyl)acetamide;
N-(4-bromophenyl)-2-((6-methyl-1H-benzo[d]imidazol-2-yl)thio)acetamide;
2-((1H-benzo[d]imidazol-2-yl)thio)-N-(4-chlorophenyl)acetamide;
N-(4-ethylphenyl)-2-((6-methyl-1H-benzo[d]imidazol-2-yl)thio)acetamide;
N-(2,4-dimethoxyphenyl)-2-((6-nitro-1H-benzo[d]imidazol-2-yl)thio)acetamide;
2-(benzo[d]oxazol-2-ylthio)-N-phenylacetamide;
2-((1H-benzo[d]imidazol-2-yl)thio)-N-phenylacetamide;
2-((1H-benzo[d]imidazol-2-yl)thio)-N-(2-methoxyphenyl)acetamide;
2-((1H-benzo[d]imidazol-2-yl)thio)-N-(3-(methylthio)phenyl)acetamide;
2-((1H-benzo[d]imidazol-2-yl)thio)-N-(4-nitrophenyl)acetamide;
2-((1H-benzo[d]imidazol-2-yl)thio)-N-(4-isopropylphenyl)acetamide;
2-((1H-benzo[d]imidazol-2-yl)thio)-N-(4-bromophenyl)acetamide;
2-((1H-benzo[d]imidazol-2-yl)thio)-N-(4-chlorophenyl)acetamide;
2-((1H-benzo[d]imidazol-2-yl)thio)-N-(3,4-dichlorophenyl)acetamide;
N-(4-ethylphenyl)-2-((6-methyl-1H-benzo[d]imidazol-2-yl)thio)acetamide;
N-(4-bromophenyl)-2((6-methyl-1H-benzo[d]imidazol-2-yl)thio)acetamide;
N-(3,4-dichlorophenyl)-2-((6-methoxy-1H-benzo[d]imidazol-2-yl)thio)acetamide;
2-((6-acetamido-1H-benzo[d]imidazol-2-yl)thio)-N-(4-iodophenyl)acetamide;
2,2,2-trifluoro-N-(2-((2-((4-iodophenyl)amino)-2-oxoethyl)thio)-1H-benzo[d]imidazol-6-yl)acetamide;
2-((6-nitro-1H-benzo[d]imidazol-2-yl)thio)-N-phenylacetamide;
N-(2-methoxyphenyl)-2-((6-nitro-1H-benzo[d]imidazol-2-yl)thio)acetamide;
N-(4-methoxyphenyl)-2-((6-nitro-1H-benzo[d]imidazol-2-yl)thio)acetamide;
N-(2,4-dimethoxyphenyl)-2-((6-nitro-1H-benzo[d]imidazol-2-yl)thio)acetamide;
N-(benzo[d][1,3]dioxol-5-yl)-2-((6-nitro-1H-benzo[d]imidazol-2-yl)thio)acetamide;
2-((6-nitro-1H-benzo[d]imidazol-2-yl)thio)-N-(p-tolypacetamide;
2-((6-nitro-1H-benzo[d]imidazol-2-yl)thio)-N-(4-(trifluoromethoxy)phenyl)acetamide;
N-(4-cyanophenyl)-2-((6-nitro-1H-benzo[d]imidazol-2-yl)thio)acetamide;
N-(4-bromophenyl)-2-((6-nitro-1H-benzo[d]imidazol-2-yl)thio)acetamide;
N-(4-chlorophenyl)-2-((6-nitro-1H-benzo[d]imidazol-2-yl)thio)acetamide;
N-(4-iodophenyl)-2-((6-nitro-1H-benzo[d]imidazol-2-yl)thio)acetamide; and
2-((6-nitro-1H-benzo[d]imidazol-2-yl)thio)-N-(4-phenoxyphenyl)acetamide, or a pharmaceutically acceptable salt thereof.

In another aspect, the present disclosure features a method of treating a bacterial infection in a subject comprising, administering to the subject a therapeutically effective amount of a compound of Formula I-c:

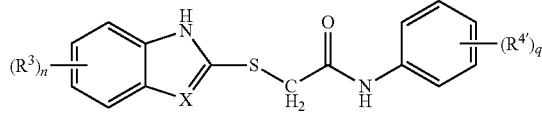

Formula I-c or a pharmaceutically acceptable salt thereof, wherein:
X is O or N;
$R^3$ is H, $C_{1-6}$ alkyl, $C_{1-6}$ alkoxy, —$NO_2$, —$NHC(O)R^c$;
$R^{4'}$ is H, bromo, chloro, $C_{1-6}$ alkyl, $C_{1-6}$ alkoxy, aryloxy, $C_{1-6}$ haloalkyl, —CN, —$NO_2$, —$SR^a$; or 2 $R^4$ together with the carbon atoms to which they are attached form a heteroaryl or heterocycloalkyl;
$R^a$ is H or $C_{1-6}$ alkyl;
$R^c$ is H, $C_{1-6}$ alkyl, $C_{1-6}$ haloalkyl; and
n and q are each independently 1, 2, 3, 4, or 5.

In some embodiments, $R^{4'}$ is H, $C_{1-6}$ alkyl, $C_{1-6}$ alkoxy, aryloxy, $C_{1-6}$ haloalkyl, —CN, —$NO_2$, and —$SR^a$.

In some embodiments, the compound is:
2-((1H-benzo[d]imidazol-2-yl)thio)-N-(4-cyanophenyl)acetamide;
2-((1H-benzo[d]imidazol-2-yl)thio)-N-(3-(methylthio)phenyl)acetamide;
N-(4-bromophenyl)-2((6-methyl-1H-benzo[d]imidazol-2-yl)thio)acetamide;
2-((1H-benzo[d]imidazol-2-yl)thio)-N-(4-chlorophenyl)acetamide;

N-(4-ethylphenyl)-2-((6-methyl-1H-benzo[d]imidazol-2-yl)thio)acetamide;
N-(2,4-dimethoxyphenyl)-2-((6-nitro-1H-benzo[d]imidazol-2-yl)thio)acetamide;
2-(benzo[d]oxazol-2-ylthio)-N-phenylacetamide;
2-((1H-benzo[d]imidazol-2-yl)thio)-N-phenylacetamide;
2-((1H-benzo[d]imidazol-2-yl)thio)-N-(2-methoxyphenyl)acetamide;
2-((1H-benzo[d]imidazol-2-yl)thio)-N-(3-(methylthio)phenyl)acetamide;
2-((1H-benzo[d]imidazol-2-yl)thio)-N-(4-nitrophenyl)acetamide;
2-((1H-benzo[d]imidazol-2-yl)thio)-N-(4-isopropylphenyl)acetamide;
2-((1H-benzo[d]imidazol-2-yl)thio)-N-(4-bromophenyl)acetamide;
2-((1H-benzo[d]imidazol-2-yl)thio)-N-(4-chlorophenyl)acetamide;
2-((1H-benzo[d]imidazol-2-yl)thio)-N-(3,4-dichlorophenyl)acetamide;
N-(4-ethylphenyl)-2-((6-methyl-1H-benzo[d]imidazol-2-yl)thio)acetamide;
N-(4-bromophenyl)-2((6-methyl-1H-benzo[d]imidazol-2-yl)thio)acetamide;
N-(3,4-dichlorophenyl)-2-((6-methoxy-1H-benzo[d]imidazol-2-yl)thio)acetamide;
2-((6-acetamido-1H-benzo[d]imidazol-2-yl)thio)-N-(4-iodophenyl)acetamide;
2,2,2-trifluoro-N-(2-((2-((4-iodophenyl)amino)-2-oxoethyl)thio)-1H-benzo[d]imidazol-6-yl)acetamide;
2-((6-nitro-1H-benzo[d]imidazol-2-yl)thio)-N-phenylacetamide;
N-(2-methoxyphenyl)-2-((6-nitro-1H-benzo[d]imidazol-2-yl)thio)acetamide;
N-(4-methoxyphenyl)-2-((6-nitro-1H-benzo[d]imidazol-2-yl)thio)acetamide;
N-(2,4-dimethoxyphenyl)-2-((6-nitro-1H-benzo[d]imidazol-2-yl)thio)acetamide;
N-(benzo[d][1,3]dioxol-5-yl)-2-((6-nitro-1H-benzo[d]imidazol-2-yl)thio)acetamide;
2-((6-nitro-1H-benzo[d]imidazol-2-yl)thio)-N-(p-tolyp acetamide;
2-((6-nitro-1H-benzo[d]imidazol-2-yl)thio)-N-(4-(trifluoromethoxy)phenyl)acetamide;
N-(4-cyanophenyl)-2-((6-nitro-1H-benzo[d]imidazol-2-yl)thio)acetamide;
N-(4-bromophenyl)-2-((6-nitro-1H-benzo[d]imidazol-2-yl)thio)acetamide;
N-(4-chlorophenyl)-2-((6-nitro-1H-benzo[d]imidazol-2-yl)thio)acetamide; and
2-((6-nitro-1H-benzo[d]imidazol-2-yl)thio)-N-(4-phenoxyphenyl)acetamide, or a pharmaceutically acceptable salt thereof.

Also provided herein are pharmaceutical compositions comprising a compound of Formula I-c as described herein, and a pharmaceutically acceptable carrier.

In some embodiments, the bacterial infection or antibiotic-tolerant infection is caused by a Gram-negative bacterium.

In an embodiment of any of the methods of the invention, the microbial infection is the result of a pathogenic bacterial infection, fungal infection, or viral infection. Examples of pathogenic bacteria include, without limitation, bacteria within the genuses *Aerobacter, Aeromonas, Acinetobacter, Agrobacterium, Bacillus, Bacteroides, Bartonella, Bortella, Brucella, Burkholderia Calymmatobacterium, Campylobacter, Citrobacter, Clostridium, Corynebacterium, Enterobacter, Escherichia, Francisella, Haemophilus, Hafnia, Helicobacter, Klebsiella, Legionella, Listeria, Morganella, Moraxella, Proteus, Providencia, Pseudomonas, Salmonella, Serratia, Shigella, Staphylococcus, Streptococcus, Treponema, Xanthomonas, Vibrio*, and *Yersinia*. Specific examples of such bacteria include *Vibrio harveyi, Vibrio cholerae, Vibrio parahemolyticus, Vibrio alginolyticus, Pseudomonas phosphoreum, Pseudomonas aeruginosa, Yersinia enterocolitica, Escherichia coli, Salmonella typhimurium, Haemophilus influenzae, Helicobacter pylori, Bacillus subtilis, Borrelia burgfdorferi, Neisseria meningitidis, Neisseria gonorrhoeae, Yersinia pestis, Campylobacter jejuni, Deinococcus radiodurans, Mycobacterium tuberculosis, Enterococcus faecalis, Streptococcus pneumoniae, Streptococcus pyogenes, K. pneumonia, A. baumannii* and *Staphylococcus aureus*.

In some embodiments, the gram-negative bacterium is a *Pseudomonas*, e.g., *P. aeruginosa*, *Kelbsiella*, e.g., *K. pneumonia*, or *Acinetobacter*, e.g., *A. baumanni*. In some embodiments, the gram-negative bacterium is *Burkholderia* species.

In some embodiments, the infection is a polymicrobial infection, e.g., an infection comprising more than one organism. In some embodiments, the infection comprises at least one of the organisms listed above, e.g., one or more of *Pseudomonas*, e.g., *P. aeruginosa*, *Kelbsiella*, e.g., *K. pneumonia*, and/or *Acinetobacter*, e.g., *A. baumanni*.

In some embodiments, the methods further include administering an antibiotic selected from the group consisting of: penicillins, cephalosporins, carbacephems, cephamycins, carbapenems, monobactams, quinolones, tetracyclines, aminoglycosides, macrolides, glycopeptides, chloramphenicols, glycylcyclines, licosamides, lipopeptides, oxazolidinones and fluoroquinolones.

In some embodiments, the bacterial infection is pneumonia, septic shock, urinary tract infection, a gastrointestinal infection, or an infection of the skin and soft tissue.

In some embodiments, the subject is a mammal, e.g., a human or non-human mammal, or plant. In some embodiments, the methods include treating one or more cells, e.g., cells in a culture dish.

In one aspect, the present disclosure features a method of treating a Gram negative infection in a subject, the method comprising administering to said subject in need of such treatment a therapeutically effective amount of a compound described herein.

In some embodiments, the Gram negative infection is caused by *Pseudomonas aeruginosa*.

In some embodiments, the subject is a trauma patient or a burn patient suffering from a burn or skin wound.

In a further aspect, the present disclosure features a method of reducing bacterial tolerance in a subject, the method comprising administering to said subject a therapeutically effective amount of a compound described herein.

In some embodiments, the method further includes identifying said subject suffering from a bacteria tolerant infection.

In some embodiments, the method further includes co-administering to said subject an antibiotic.

In some embodiments, the antibiotic is a quinolone antibiotic.

By virtue of their design, the compositions and methods described herein possess certain advantages and benefits. First, the compounds described herein can target virulence factor production and therefore decrease the incidence of resistance. Second, the compounds described herein target factors specific to pathogens (e.g., *P. aeruginosa*) and therefore do not kill beneficial commensal bacteria. Additionally, the compounds described herein can treat both acute infections as well as chronic infections that plague immune-compromised individuals.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 2A-2M are tables showing the effect of compounds on 4-hydroxy-2-alkylquinoline (HAQ) levels, including the MvfR ligands 4-hydroxy-2-heptylquinoline (HHQ) and 3,4-dihydroxy-2-heptylquinoline (PQS), as well as 2-n-heptyl-4-hydroxyquinoline-N-oxide (HQNO) and 2,4-dihydroxyquinoline (DHQ). Levels of the phenazine, pyocyanin, were also determined, as were levels of anthranilic acid (AA) and 2-amino acetophenon (2-AA).

FIGS. 3A-3C and 4 are tables showing the effect of compounds tested on HAQ, PQS, HQNO, and pyocyanin levels.

DETAILED DESCRIPTION

Figure 1:
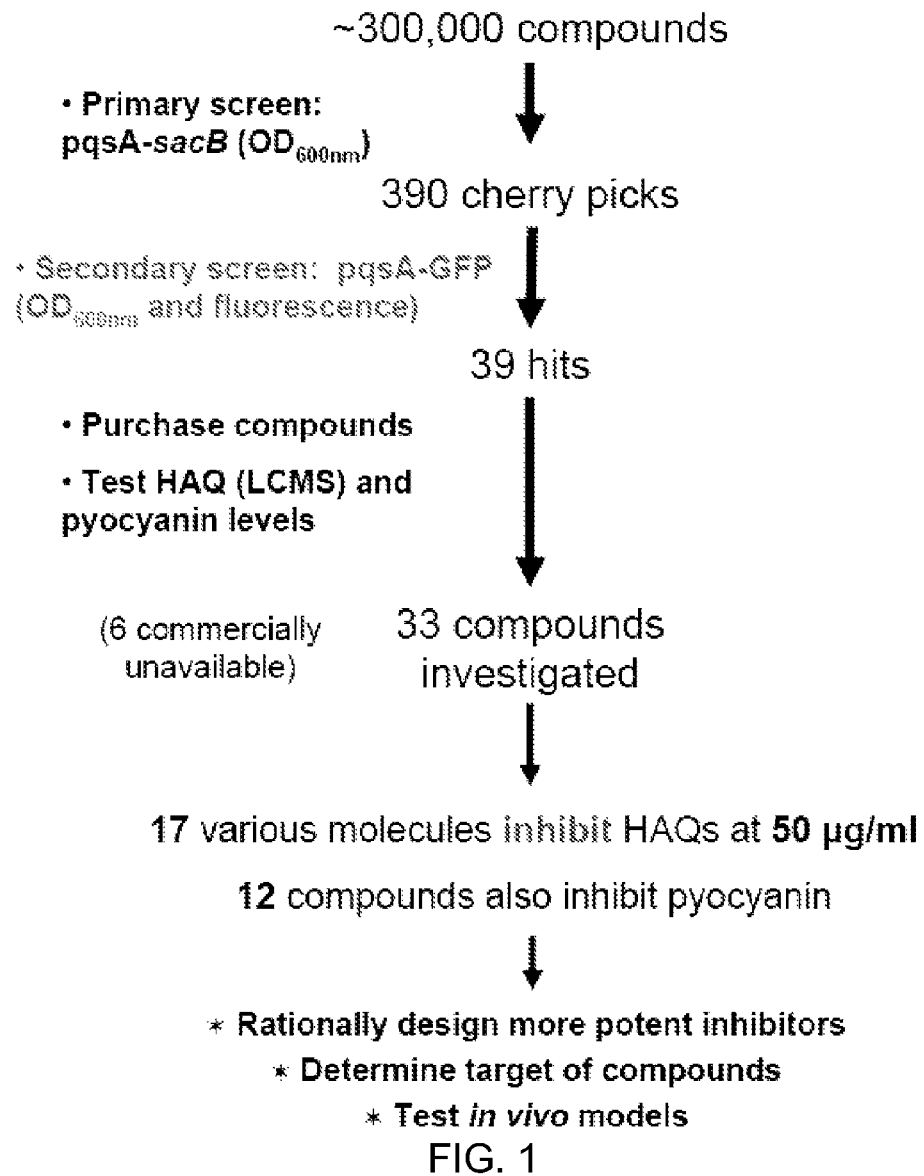
FIG. 1 is a diagram showing how the MvfR inhibitors were chosen.

The present disclosure provides, inter alia, compositions and methods for treating and/or preventing an infection caused by a pathogen such as a bacterium (e.g. *Pseudomonas aeruginosa*) by blocking bacterial virulence mechanisms and pathogenesis in vivo. Population density-dependent signaling, generally referred to as quorum sensing (QS), is one such mechanism. QS is a cell-cell signaling density-dependent communication system that is achieved through the production and regulation of low molecular weight molecules as a means to activate virulence factors critical for full virulence in mammals and regulation of multiple aspects of virulence. It is important for the development of acute infections as well as for the formation of antibiotic-tolerant cell populations, a process underlying pathogen persistence in chronic infections. Bacteria cells that are able to tolerate antibiotic killing and host defense mechanisms can persist in the body and provide a reservoir for re-initiation of infection. Etiological agents of some serious chronic infections are often refractory to antibiotics due to antibiotic tolerance, and are therefore very difficult to treat.

QS signaling circuits are evolutionarily conserved and play central roles in modulating virulence mechanisms in many different human pathogens. For example, without wishing to be bound by theory, the compounds described herein may target the QS cell-to-cell signaling systems used by many pathogens to communicate and activate multiple virulence factors. The QS systems of the Gram-negative bacterium *Pseudomonas aeruginosa*, have been recognized for their importance in virulence and thus can serve as an excellent target for the development of novel therapeutics that are urgently needed.

*P. aeruginosa* is a recalcitrant Gram-negative bacterium that defies eradication by antibiotics and exemplifies current problematic pathogens in hospitals and intensive care units. This pathogen causes difficult to treat infections such as urinary tract infections, respiratory system infections, dermatitis, soft tissue infections, bacteremia and a variety of systemic infections, particularly in victims of severe burns and individuals with cystic fibrosis, cancer, and AIDS who are immunosuppressed.

*P. aeruginosa* QS regulated virulence functions are controlled by the low molecular weight signaling molecules, acyl-homoserine lactones (HSL) 3-oxo-C12-HSL and C4-HSL produced through the Las and Rh1 systems; and by the 4-hydroxy-2-alkylquinolines (HAQs) produced through the MvfR system. The compounds described herein can inhibit the production of the low molecular weight compounds, HAQs, and thus QS signaling that controls virulence and antibiotic tolerance.

Conventional antibiotics target a narrow spectrum of activities that are essential for bacterial growth in culture. Pharmacological targeting of non-essential functions such as virulence factor production through inhibition of QS signaling may decrease the incidence of resistance since bacterial growth per se is not directly challenged and subjected to selection pressure.

Thus, QS systems are suitable targets for new antimicrobials, since they are not imperative for bacterial growth or survival, and they play important roles in pathogenesis. As such, there exists a need for new antimicrobial compounds which target virulence factor production and antibiotic tolerance. The compounds described herein help fulfill these and other needs.

Compounds

At various places in the present specification, substituents of compounds of the invention are disclosed in groups or in ranges. It is specifically intended that the invention include each and every individual sub-combination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

For compounds of the invention in which a variable appears more than once, each variable can be a different moiety selected from the Markush group defining the variable. For example, where a structure is described having two R groups that are simultaneously present on the same compound; the two R groups can represent different moieties selected from the Markush group defined for R. In another example, when an optionally multiple substituent is designated in the form:

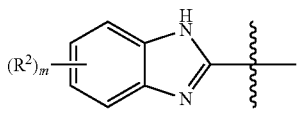

then it is understood that substituent $R^2$ can occur m number of times on the ring, and $R^2$ can be a different moiety at each occurrence.

As used herein, the term "substituted" or "substitution" refers to the replacement of a hydrogen atom with a moiety other than H. For example, an "N-substituted piperidin-4-yl" refers to the replacement of the piperidinyl NH with a non-hydrogen substituent, such as alkyl. In another example, a "4-substituted phenyl" refers to replacement of the H atom on the 4-position of the phenyl with a non-hydrogen substituent, such as chloro.

It is further intended that the compounds of the invention are stable. As used herein "stable" refers to a compound that is sufficiently robust to survive isolation to a useful degree of purity from a reaction mixture, and preferably capable of formulation into an efficacious therapeutic agent.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable sub-combination.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms. The term "alkylenyl" refers to a divalent alkyl linking group.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "aryloxy" refers to an —O-aryl group. An example aryloxy group is phenoxy.

As used herein, "cycloalkyl" refers to non-aromatic cyclic hydrocarbons including cyclized alkyl, alkenyl, and alkynyl groups. Cycloalkyl groups can include mono- or polycyclic (e.g., having 2, 3 or 4 fused rings) ring systems as well as 2-ring, 3-ring, 4-ring spiro system (e.g., having 8 to 20 ring-forming atoms). Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo, pyrido or thieno derivatives of pentane, pentene, hexane, and the like. Carbon atoms of the cycloalkyl group can be optionally oxidized, e.g. bear an oxo or sulfildo group to form CO or CS.

As used herein, "heteroaryl" groups refer to an aromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heterocycloalkyl" refers to non-aromatic heterocycles including cyclized alkyl, alkenyl, and alkynyl groups where one or more of the ring-forming carbon atoms are replaced by a heteroatom such as an O, N, or S atom. Also included in the definition of heterocycloalkyl are moieties that have one or more aromatic rings fused (i.e., having a bond in common with) to the nonaromatic heterocyclic ring, for example phthalimidyl, naphthalimidyl, and benzo derivatives of heterocycles such as indolene and isoindolene groups. Heterocycloalkyl groups can be mono- or polycyclic (e.g., having 2, 3, 4 or more fused rings or having a 2-ring, 3-ring, 4-ring spiro system (e.g., having 8 to 20 ring-forming atoms)). Heteroatoms or carbon atoms of the heterocycloalkyl group can be optionally oxidized, e.g., bearing one or two oxo or sulfildo groups to form SO, $SO_2$, CO, NO, etc. In some embodiments, the heterocycloalkyl group has from 1 to about 20 carbon atoms, and in further embodiments from about 3 to about 20 carbon atoms. In some embodiments, the heterocycloalkyl group contains 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds. Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, as well as radicals of 3H-isobenzofuran-1-one, 1,3-dihydro-isobenzofuran, 2,3-dihydro-benzo[d]isothiazole 1,1-dioxide, and the like.

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used here, "haloalkoxy" refers to an —O-haloalkyl group. An example haloalkoxy group is $OCF_3$.

As used herein, "arylalkyl" refers to alkyl substituted by aryl and "cycloalkylalkyl" refers to alkyl substituted by cycloalkyl. An example arylalkyl group is benzyl.

As used herein, "amino" refers to $NH_2$.

As used herein, "alkylamino" refers to an amino group substituted by an alkyl group.

As used herein, "dialkylamino" refers to an amino group substituted by two alkyl groups.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms, such as keto-enol tautomers.

Compounds of the invention can also include all isotopes of atoms occurring in the intermediates or final compounds. Isotopes include those atoms having the same atomic number but different mass numbers. For example, isotopes of hydrogen include tritium and deuterium.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like.

The pharmaceutically acceptable salts of the present invention include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

The present disclosure also includes prodrugs of the compounds described herein. As used herein, "prodrugs" refer to any covalently bonded carriers which release the active parent drug when administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the invention. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Synthesis

Compounds of the present disclosure, including salts, hydrates, and solvates thereof, can be prepared using known organic synthesis techniques and can be synthesized according to any of numerous possible synthetic routes, e.g., as described herein.

Reactions for preparing compounds of the present disclosure can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Preparation of compounds of the disclosure can involve the protection and deprotection of various chemical groups. The need for protection and deprotection, and the selection of appropriate protecting groups can be readily determined by one skilled in the art. The chemistry of protecting groups can be found, for example, in T. W. Green and P. G. M. Wuts, *Protective Groups in Organic Synthesis*, 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Example synthetic routes to compounds of the invention are provided in Scheme 1 below, where constituent members of the depicted formulae are defined herein.

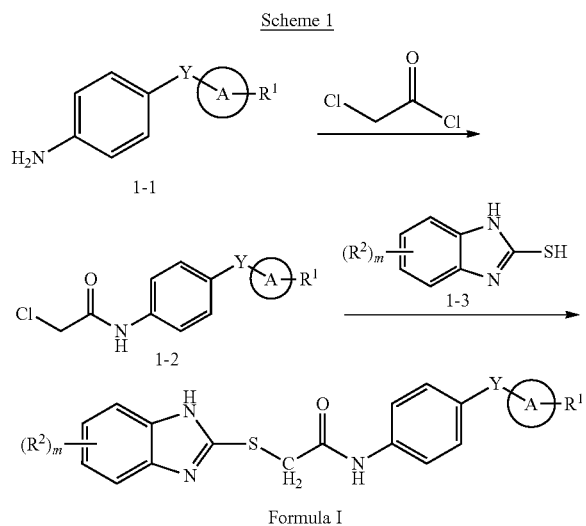

Scheme 1

Compounds of the invention can be assembled as shown in Scheme 1. Functionalized anilines of Formula 1-1 can be reacted with chloroacetyl chloride in the presence of a base to produce the chloro-acetamide compounds of Formula 1-2. Subsequent reaction with thiobenzimidazoles of Formula 1-3 in the presence of a base yields compounds of Formula I.

Methods of Treatment

The present disclosure provides methods for treating and preventing acute and chronic infections by administering to a subject a therapeutically effective amount of a compound described herein. For example, the compounds described herein can be used to treat an acute infection caused by a pathogen and, as a result of treatment, shut down the infection. In addition, the compounds described herein can be used to treat chronic, persistent infections caused by pathogens such as bacteria (e.g., gram negative bacteria, e.g., *P. auruginosa*) that have become tolerant to antibiotic treatment, e.g., as a result of activation of a QS system. The compounds described herein can treat individuals suffering from such chronic infections, e.g., by targeting the virulence factor pathways of these tolerant bacteria. In general the methods can be used to treat any organism that is susceptible to bacterial infections, e.g., animals, including mammals, e.g., humans and non-human mammals, as well as plants.

Patients suitable for such treatment may be identified by methods known in the art, e.g., by the detection of symptoms commonly associated with infection, such as fever, pain, pus, culture of organisms, and the like. Infections that can be treated with the compounds described herein include those caused by or due to pathogens. In some embodiments, the pathogen is a bacterium (e.g., a gram-negative bacterium, e.g., *Pseudomonas*, e.g., *P. aeruginosa*).

Clinical indications can include, but are not limited to: 1) burn and/or wound infections; 2) nosocomial pneumonia; 3) cystic fibrosis; 4) osteomyelitis; and 5) sepsis in an immuno- suppressed host. In some embodiments, the subject has an acute infection. In some embodiments, the subject has a chronic infection. A chronic infection can last three weeks or more, or if the infection is recurrent despite completion of antibiotic treatment. In some embodiments, the following pathogenic infections are treated using the compounds described herein.

Invasive burn wound infections remains the most common cause of morbidity and mortality in extensively burned subjects. Infection is the predominant determinant of wound healing, incidence of complications, and outcome of burn subjects. The main organisms responsible are *Pseudomonas aeruginosa, S. aureus, Streptococcus pyogenes*, and various Gram-negative organisms.

Nosocomial pneumonias account for nearly 20% of all nosocomial infections. Subjects most at risk for developing nosocomial pneumonia are those in intensive care units, subjects with altered levels of consciousness, elderly subjects, subjects with chronic lung disease, ventilated subjects, smokers and post-operative subjects. In a severely compromised subject, multiantibiotic-resistant nosocomial pathogens are likely to be the cause of the pneumonia. The main organisms responsible are *P. aeruginosa, S. aureus, Klebsiella pneumoniae* and *Enterobacter* spp.

Cystic fibrosis (CF) is the most common genetic disorder of the Caucasian population. Pulmonary disease is the most common cause of premature death in cystic fibrosis subjects. Optimum antimicrobial therapy for CF is not known, and it is generally believed that the introduction of better anti-pseudomonal antibiotics has been the major factor contributing to the increase in life expectancy for CF subjects. The most common organisms associated with lung disease in CF are *S. aureus, P. aeruginosa* and *H. influenzae. P. aeruginosa* is the leading pathogen.

Osteomyelitis causes the vascular supply to the bone to be compromised by infection extending into surrounding tissue. Within this necrotic and ischemic tissue, the bacteria may be difficult to eradicate even after an intense host response, surgery, and/or antibiotic therapy. The main organisms responsible are *S. aureus, E. coli*, and *P. aeruginosa*.

Treatment of infections in subjects who are immune-compromised by virtue of chemotherapy-induced granulocytopenia and immunosuppression related to organ or bone marrow transplantation can be a challenge. Neutropenic subjects are especially susceptible to bacterial infection. Organisms likely to cause infections in granulocytopenic subjects are: *S. epidermidis, S. aureus, S. viridans, Enterococcus* spp, *E. coli, Klebsiella* spp, *P. aeruginosa* and *Candida* spp.

Small bowel bacterial overgrowth syndrome (SBBOS), or small intestinal bacterial overgrowth (SIBO), also termed bacterial overgrowth; is a disorder of excessive bacterial growth in the small intestine. Certain species of bacteria are more commonly found in aspirates of the jejunum taken from patients with bacterial overgrowth. The most common isolates are *Escherichia coli, P. aeruginosa, Streptococcus, Lactobacillus, Bacteroides*, and *Enterococcus* species. See e.g. Kopacova et al. "Small Intestinal Bacterial Overgrowth Syndrome" *World J. Gastroenterol.* 16(24): 2978-2990, 2010, which is incorporated herein by reference in its entirety. In some embodiments, the compounds described herein can be used to treat small intestinal bacterial overgrowth syndrome (SIBO).

In some embodiments, the compounds described herein can be used to preventatively treat patients undergoing endoscopy. These patients are often found to be infected by *Pseudomonas aeruginosa* after undergoing endoscopic procedures.

In some embodiments, the compounds described herein can be used in combination with an antibiotic agent. The combination may be used to affect a synergistic result, to overcome an acute or chronic infection, or overcome bacterial tolerance.

Examples of classes of antibiotics that can be used in combination with the compounds described herein include penicillins, cephalosporins, carbacephems, cephamycins, carbapenems, monobactams, quinolones, tetracyclines, aminoglycosides, macrolides, glycopeptides, chloramphenicols, glycylcyclines, licosamides, lipopeptides, oxazolidinones and fluoroquinolones.

Essential Structure of Quinolone Antibiotics

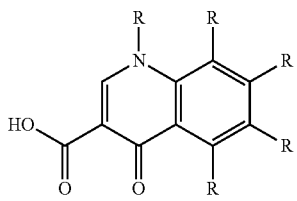

In some embodiments, the antibiotic that can be used in combination with the compounds described herein is a quinolone antibiotic. Example quinolones include without limitation cinoxacin, flumequine, nalidixic acid, oxolinic acid, piromidic acid, pipemidic acid, rosoxacin, ciprofloxacin, enoxacin, fleroxacin, lomefloxacin, nadifloxacin, norfloxacin, ofloxacin, pefloxacin, rufloxacin, balofloxacin, grepafloxacin, levofloxacin, pazufloxacin, sparfloxacin, temafloxacin, tosufloxacin, clinafloxacin, gatifloxacin, gemifloxacin, moxifloxacin, sitafloxacin, trovafloxacin, prulifloxacin, garenoxacin, delafloxacin, danofloxacin, difloxacin, enrofloxacin, ibafloxacin, marbofloxacin, orbifloxacin, and sarafloxacin.

In some embodiments, the antibiotic that can be used in combination with the compounds described herein is rifaximin to treat SIBO.

Plants

Resistance of plant pathogens to antibiotics such as oxytetracycline is rare, but the emergence of streptomycin-resistant strains of *Erwinia amylovora*, *Pseudomonas* spp., and *Xanthomonas campestris* has impeded the control of several important plant diseases.

In some embodiments, the compounds described herein can be used to treat plant bacterial diseases. As used herein, "plants" refer to photosynthetic organisms, both eukaryotic and prokaryotic. Plants include trees and shrubs (e.g., conifers), herbs, bushes (greater than 100 different families), grasses (e.g., Gramineae, Cyperaceae, and Juncaceae), vines (any number of families using any climbing method), ferns (e.g., a species from the Psilotopsida, Equisetopsida, Marattiospida or Polypodiopsida class), mosses (i.e., bryophytes), fungi (e.g. edible and/or commercially useful varieties), and green algae (e.g., unicellular, flagellates, and filamentous).

Representative species of plants that may benefit from application of the antibiotic described herein, many of which are grown around the world for agronomic purposes, include, without limitation, corn (*Zea mays*), wheat (*Triticum* spp.), rice (*Oryza* spp.), tobacco (*Nicotiana* spp.), potatoes (*Solanum tuberosum*), cotton (*Gossypium hirsutum*), rapeseed and canola (*Brassica* spp.), and sunflower (*Helianthus annus*), as well as any number of fruits (e.g., *Malus* spp., *Citrus* spp., *Vitus* spp., and *Musa* spp.) or legumes (e.g., soybean (*Glycine max*), peas (*Pisum sativum*), and beans (from the Leguminosae family)). There are a number of flowering species (e.g., species of angiosperms) not included in any of the above-indicated plants that also may benefit from application of the antibiotic described herein.

In some embodiments, the compounds described herein can be used in combination with antibiotics that are used to treat plant bacterial diseases. Examples of antibiotics that can be used in combination include, but are not limited to, streptomycin, oxytetracycline, gentamicin, and oxolinic acid. See e.g. McManus et al. "Antibiotic Use in Plant Agriculture" *Annu. Rev. Phytopathol.* 40:443-65, 2002, which is incorporated herein by reference in its entirety. See also the world-wide websites "apsnet.org/publications/apsnetfeatures/Pages/AntibioticsForPlants.aspx," "apsnet.org/edcenter/intropp/topics/Pages/PlantDiseaseManagement.aspx," and "plantmanagementnetwork.org/pub/php/review/antibiotic/" for examples of plant disease control and antibiotic usages, each of which are incorporated by reference in its entirety.

In some embodiments, the compounds are applied to the leaves of a plant (e.g., as part of a foliar spray or dust); in some embodiments, the compounds are applied to the soil surrounding a plant, or into which a plant, seed, or seedling will be placed. Compositions for use in plants can contain other agriculturally or horticulturally-acceptable or useful ingredients.

Pharmaceutical Formulations and Dosage Forms

When employed as pharmaceuticals, the compounds of the present disclosure can be administered in the form of pharmaceutical compositions. These compositions can be prepared in a manner well known in the pharmaceutical art, and can be administered by a variety of routes depending upon whether local or systemic treatment is desired and upon the area to be treated. Administration can be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or can be, for example, by a continuous perfusion pump. Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The present disclosure also includes pharmaceutical compositions which contain, as the active ingredient, one or more of the compounds described herein in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the present disclosure can be formulated so as to provide quick, sustained or delayed release of the active ingredient after administration to the subject by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compounds or compositions of the present disclosure contain from about 5 to about 50 mg of the active ingredient. One having ordinary skill in the art will appreciate that this embodies compounds or compositions containing from about 5 to about 10, from about 10 to about 15, from about 15 to about 20, from about 20 to about 25, from about 25 to about 30, from about 30 to about 35, from about 35 to about 40, from about 40 to about 45, or from about 45 to about 50 mg of the active ingredient.

In some embodiments, the compounds or compositions of the present disclosure contain from about 50 to about 500 mg of the active ingredient. One having ordinary skill in the art will appreciate that this embodies compounds or compositions containing from about 50 to about 75, from about 75 to about 100, from about 100 to about 125, from about 125 to about 150, from about 150 to about 175, from about 175 to about 200, from about 200 to about 225, from about 225 to about 250, from about 250 to about 275, from about 275 to about 300, from about 300 to about 325, from about 325 to about 350, from about 350 to about 375, from about 375 to about 400, from about 400 to about 425, from about 425 to about 450, from about 450 to about 475, or from about 475 to about 500 mg of the active ingredient.

In some embodiments, the compounds or compositions of the present disclosure contain from about 500 to about 1000 mg of the active ingredient. One having ordinary skill in the art will appreciate that this embodies compounds or compositions containing from about 500 to about 550, from about 550 to about 600, from about 600 to about 650, from about 650 to about 700, from about 700 to about 750, from about 750 to about 800, from about 800 to about 850, from about 850 to about 900, from about 900 to about 950, or from about 950 to about 1000 mg of the active ingredient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

For preparing solid compositions such as tablets, the principal active ingredient is mixed with a pharmaceutical excipient to form a solid pre-formulation composition containing a homogeneous mixture of a compound of the present disclosure. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.1 to about 1000 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present disclosure can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face mask tent, or intermittent positive pressure breathing machine. Solution, suspension, or powder compositions can be administered orally or nasally from devices which deliver the formulation in an appropriate manner.

The amount of compound or composition administered to a subject will vary depending upon what is being administered, the purpose of the administration, such as prophylaxis or therapy, the state of the subject, the manner of administration, and the like. In therapeutic applications, compositions can be administered to a subject already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the subject, and the like.

The compositions administered to a subject can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present disclosure can vary according to, for example, the particular use for which the treatment is made, the manner of administration of the compound, the health and condition of the subject, and the judgment of the prescribing physician. The proportion or concentration of a compound of the present disclosure in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular subject, the relative biological efficacy of the compound selected, formulation of the excipient, and its route of administration. Effective doses can be extrapolated from dose-response curves derived from in vitro or animal model test systems.

The compounds of the present invention can also be formulated in combination with one or more additional active ingredients which can include any pharmaceutical agent such as antibodies, immune suppressants, anti-inflammatory agents, chemotherapeutics, or drugs used for the treatment of a bacterial infection and the like.

Kits

The present disclosure also includes pharmaceutical kits useful, for example, in the treatment or prevention of acute and chronic infections which include one or more containers containing a pharmaceutical composition comprising a therapeutically effective amount of a compound of the present disclosure. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

EXAMPLES

The present disclosure will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1

2-((6-nitro-1H-benzo[d]imidazol-2-yl)thio)-N-(4-phenoxyphenyl)acetamide

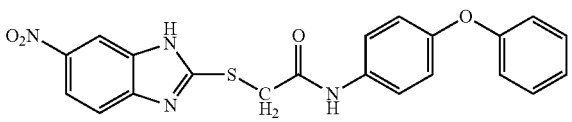 [SMILES: O=C(CSc1nc2ccc([N+](=O)[O-])cc2[nH]1)Nc1ccc(Oc2ccccc2)cc1]

To 3.55 g of 4-phenoxyaniline in 40 ml of methylene chloride containing 2.9 ml of triethylamine is added 1.6 ml of chloroacetyl choride in 20 ml of methylene chloride. After two hours at room temperature, the mixture is extracted with water to yield 2.74 g of N-(4-phenoxyphenyl)-2-chloro-acetamide.

To 2.74 g of N-(4-phenoxyphenyl)-2-chloro-acetamide in 180 ml of a 1M NaOH solution containing 130 ml of MeOH and 60 mL of water is added 2.06 g of 6-nitro-2-thiobenzimidazole and the mixture is heated at 70° C. for 3 h. The mixture is extracted with ethyl acetate and washed with 0.5M NaOH. The oily residue is recrystallized in ethyl acetate and hexane to produce 0.138 g of N-(4-methoxyphenyl)-2-((6-nitro-1H-benzo[d]imidazol-2-yl)thio)acetamide. [M+H$^+$]=421, MS/MS 236 and 208

Example 2

High Throughput Screening (HTS) of 284,256 Compounds

A Bacterial Cell Growth Assay Aids in the Discovery of Anti-Virulence Compounds

Experiments were performed to identify compounds that inhibit the MvfR regulon without altering growth, ultimately attenuating P. aeruginosa infection. MvfR is a LysR-type transcriptional regulator that directs HAQs synthesis, including that of its ligands, 4-hydroxy-2-heptylquinoline (HHQ) and 3,4-dihydroxy-2-heptylquinoline (PQS). MvfR regulates the production of many virulence factors including pyocyanin, elastase, and lectins as well as a myriad of low molecular weight molecules; and both MvfR and PQS have been demonstrated as essential for pathogenesis in several host models.

MvfR promotes the production of HAQs by binding to and activating the pqs operon, which encodes enzymes for HAQ synthesis. Anthranilic acid (AA), derived from the phnAB, kynABU, and trpEG pathways, is the precursor for HAQs. pqsA encodes an anthranilate-coenzyme A ligase, which activates anthranilic acid and catalyzes the first committed step to HAQ production. The exact roles of PqsB and PqsC are unknown, though both show homology to acyl-carrier-proteins and both are required for HHQ and PQS production. PqsD is a condensing enzyme that along with PqsA has been shown to be necessary and sufficient for the production of 2,4-dihydroxyquinoline (DHQ), a molecule whose biological role has yet to be determined. The final gene of the operon, pqsE encodes for a putative hydrolase, and while the protein is not required for the synthesis of HAQs, it is necessary for pyocyanin production.

To generate a biological reporter assay suitable for HTS, the fact that ligand-bound MvfR binds to and activates the pqsA promoter was exploited. PqsA is an anthranilate-coA ligase which catalyzes the first step in the HAQ biosynthetic pathway. The pqsA promoter was fused to the *Bacillus subtilis* sacB gene and incorporated this construct stably into the PA14 chromosome. The sacB gene product levansucrase is toxic when cells are grown in the presence of sucrose, and this gene has been previously incorporated into allelic exchange vectors as a means of counter-selection. In this system, the bacteria cells die when the pqsA promoter is activated by MvfR, allowing the identification of compounds that suppress pqsA activity by measuring growth. Using a plate reader with $OD_{600nm}$ as a readout for the assay, the construct was tested and proved successful in both laboratory and pilot high-throughput settings. 4-CABA, an AA analog which has been shown to effectively inhibit MvfR was used as a positive control.

*P. aeruginosa* PA14 cultures were grown overnight and subcultured in the morning until reaching mid-logarithmic phase. Cells were centrifuged, washed and resuspended in LB+10% sucrose to a final $OD_{600nm}$ of 0.05. 30 µl of cells were aliquoted into 384-well plates using Matrix WellMate. 1.5 mM 4-CABA was added to one column as a positive control, and another column was reserved free of compound for a negative control. 300 nl of library compounds in DMSO were added to each plate via an Epson compound transfer robot, representing a final concentration of 50 µg/ml. Each library plate was screened in duplicate. After 8 hours incubating at 37° C., $OD_{600nm}$ was determined for each well using an EnVision® plate reader (Perkin-Elmer). The strength of each compound-containing well was determined by calculating its z-score.

Bacterial Strains and Growth Conditions

PA14 is the wild-type *P. aeruginosa* strain. *Burkholderia thailandensis* is closely related to *Burkholderia pseudomallei*. All strains were routinely cultured in LB at 37° C., with antibiotics where necessary: 75 µg/ml tetracycline, 100 µg/ml rifampicin, and 300 µg/ml carbenicillin.

Quantification of Pyocyanin

Pyocyanin levels were determined by measuring $OD_{520nm}$ of chloroform-extracted cultures.

LC/MS Analyses for HAQ Determination

The quantification of HAQs in bacterial culture supernatants was performed. The HAQs were separated on a C18 reverse-phase column connected to a triple quadrupole mass spectrometer, using a water/acetonitrile gradient. Positive electrospray in MRM mode with $2 \times 10^{-3}$ mTorr argon and 30 V as the collision gas and energy was employed to quantify HAQs, using the ion transitions HHQ 244>159, HHQ-D4 248>163, HQNO 260>159, PQS 260>175, and PQS-D4 264>179. *B. thailandensis* HAQs were assessed as above. The pseudomolecular ions of each compound were monitored in full scan mode, using the unsaturated PA14 HAQ response factors.

Identification of Novel Lead HAQ Inhibitors

A total of 284,256 compounds were screened in duplicate from the available libraries at the Institute of Chemistry and Cell Biology (ICCB)-Longwood screening facility (Harvard Medical School, 250 Longwood Avenue, Seeley Mudd Room 604, Boston Mass. 02115) (FIG. 1). The strength of each hit garnered in the screen was determined by calculating its z-score. This statistical analysis normalizes hits on a plate to plate basis and represents the standard deviation from the mean plate value. 532 compounds with a strong z-score were identified. The strongest hits with structures having limited potential liability based on structural analysis, 392 in total, were available as aliquots for further analyses. The most promising compounds were tested in a secondary screening assay using a reporter construct with the *Pseudomonas aeruginosa* (pqsA) promoter fused to a short half-life green fluorescent protein (GFP), screening for compounds that quench fluorescence. This construct was used to confirm the repression of pqsA, to determine the compound's influence on bacterial growth, and to rule out potential false positives, such as the possibility that the compound negatively affects SacB. Two concentrations of compounds were tested in the secondary screen, representing final concentrations of ~50 µg/ml and ~25 µg/ml, and both growth ($OD_{600}$ nm) and fluorescence were measured. A total of 33 commercially available compounds that did not impact growth and that completely eliminated fluorescence at the lower concentration were purchased for further studies.

Figure 2D:
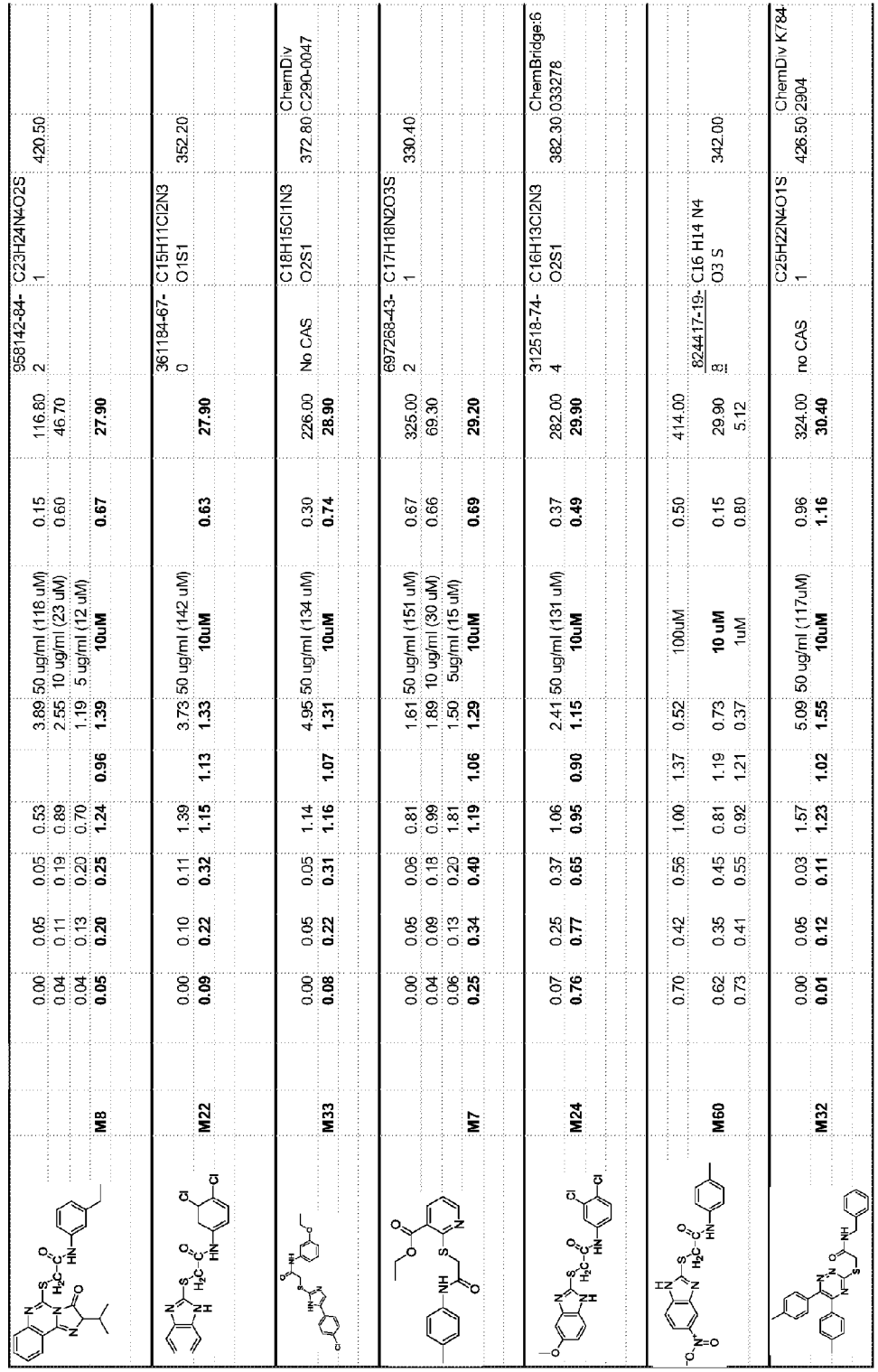
Figure 2E:
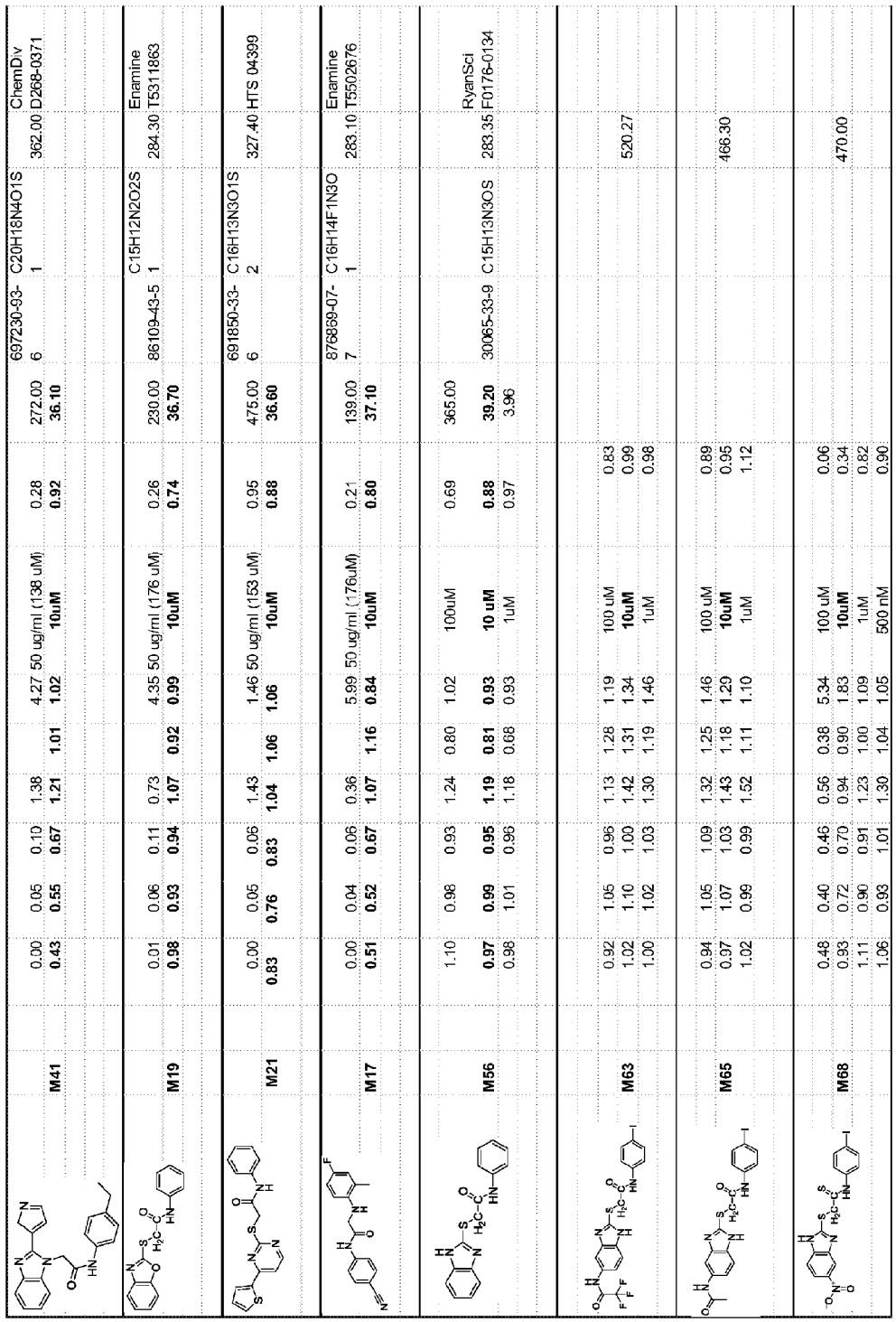
Figure 2I:
Figure 2J:
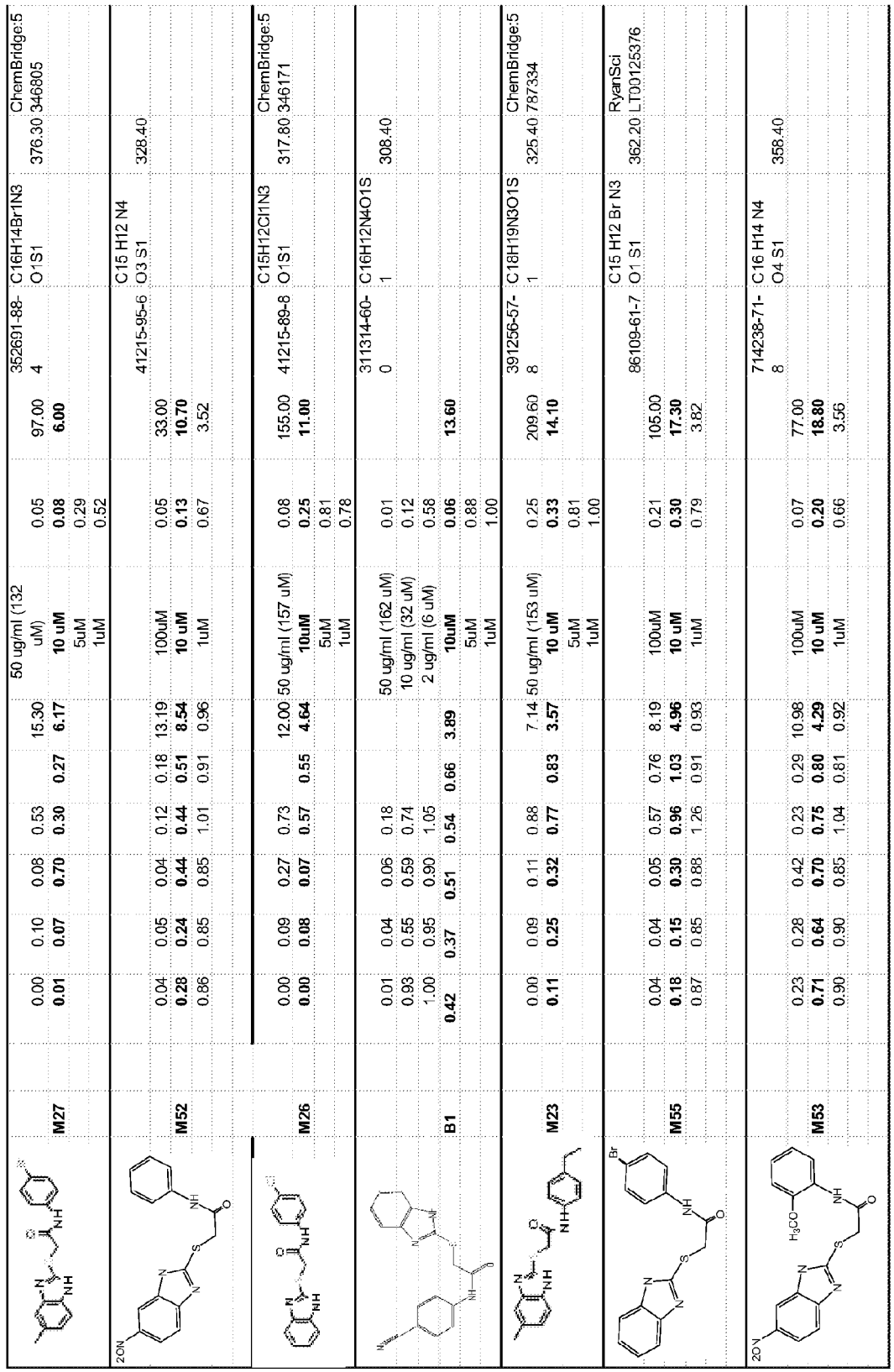
Figure 2K:
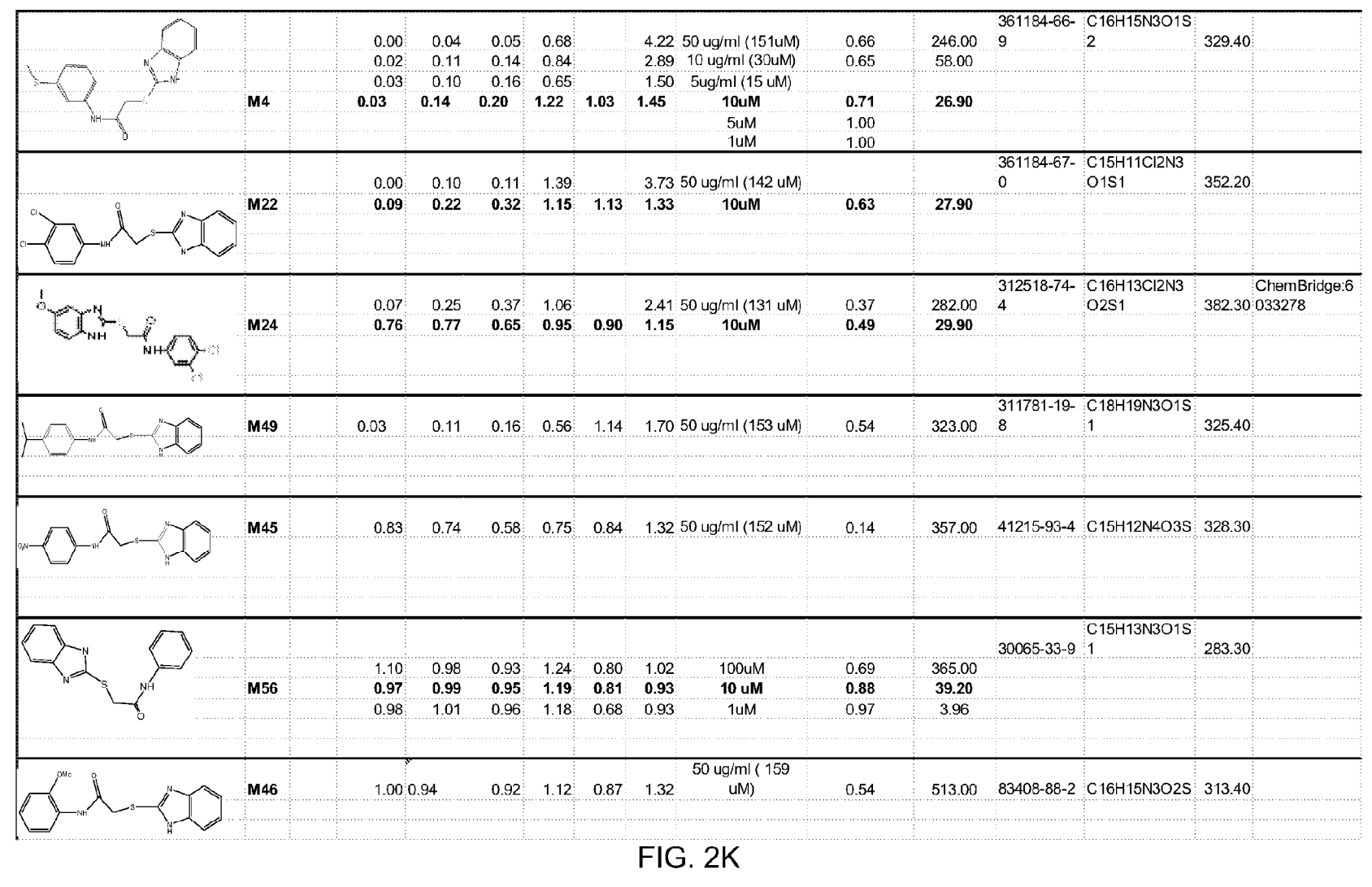
Figure 2N:
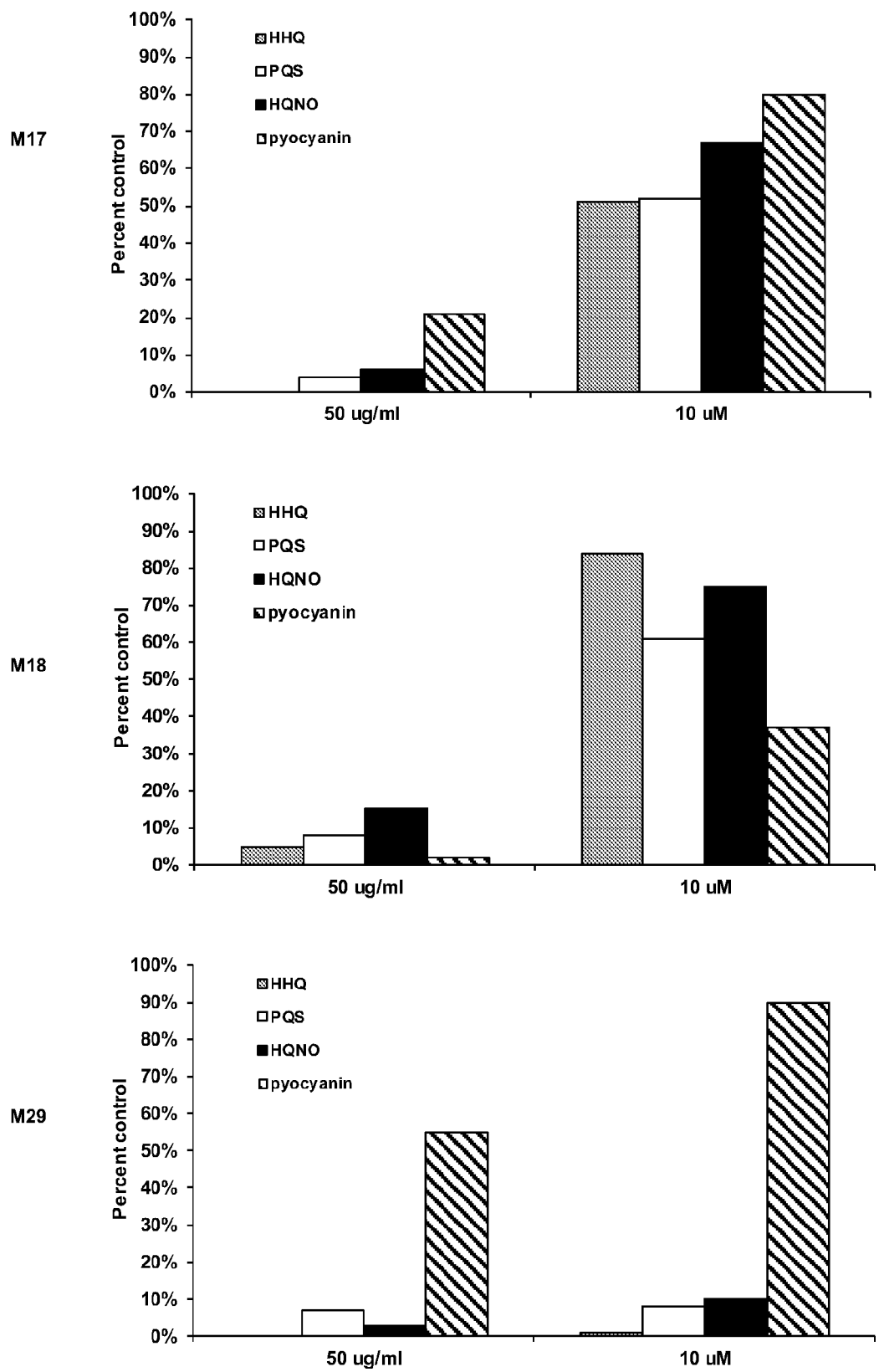
FIGS. 2N-2P are bar graphs showing the effects of selected compounds on levels of HHQ, PQS, HQNO, and pyocyanin
Figure 2O:
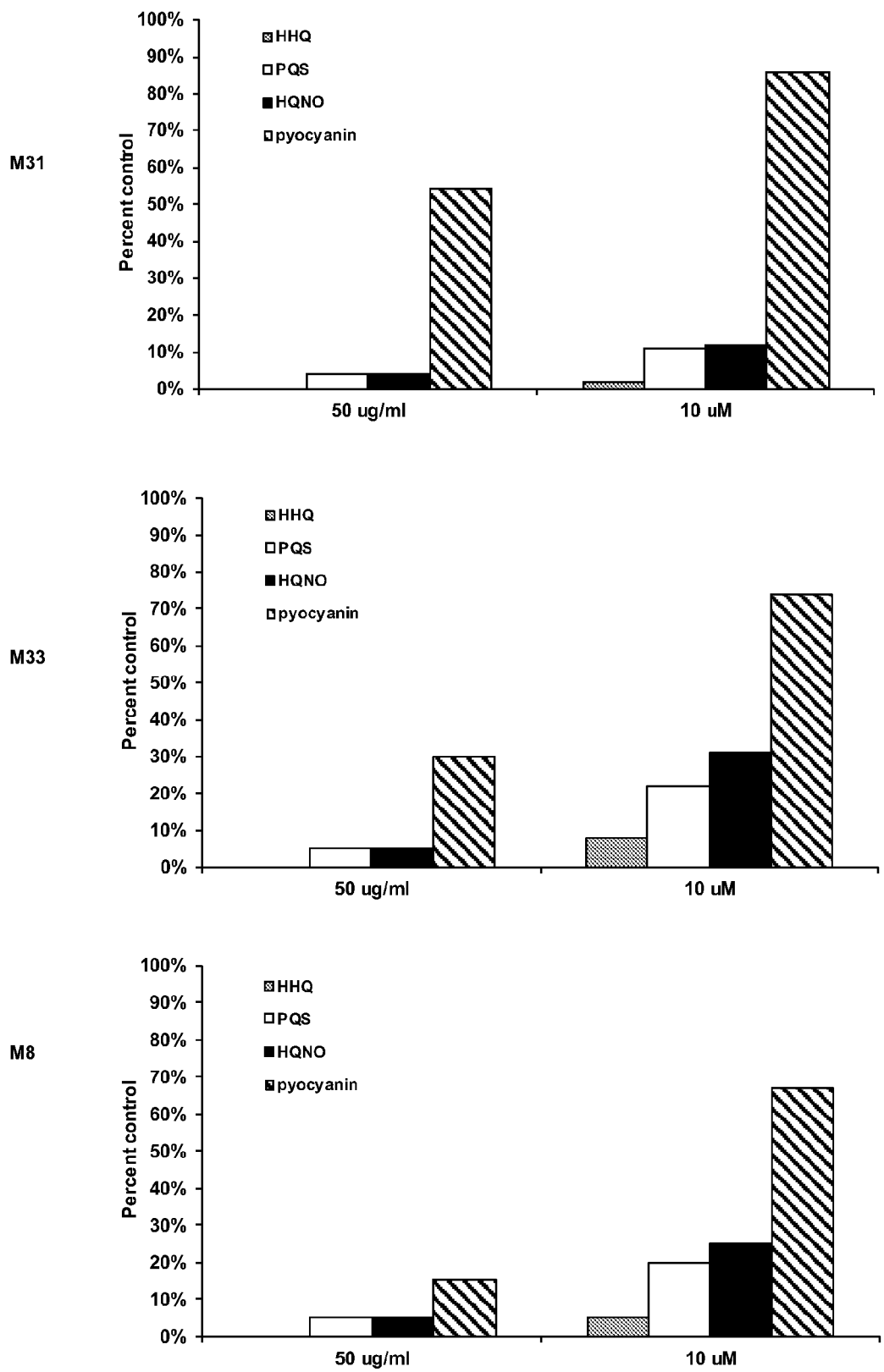
Figure 2P:
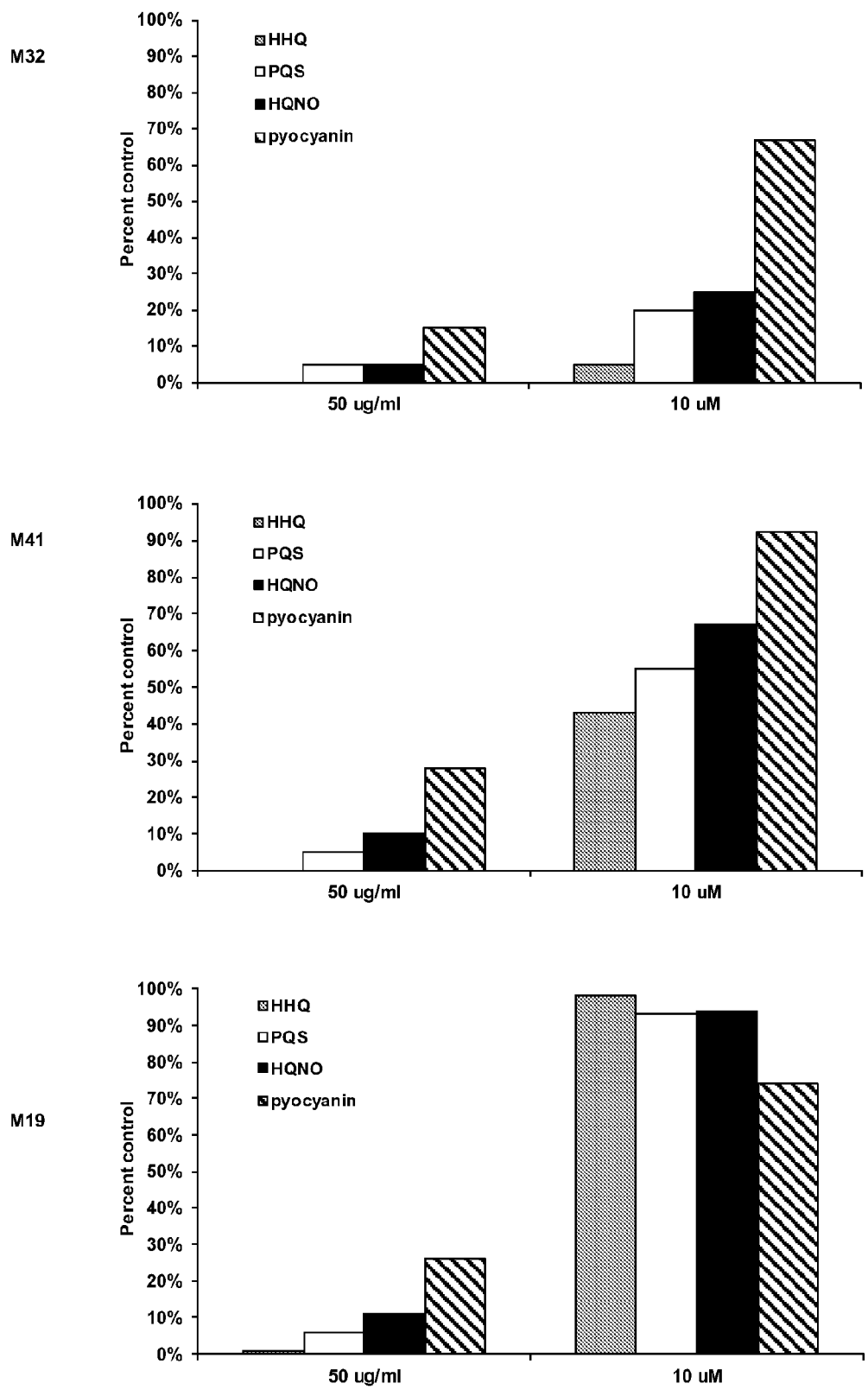
Figure 3A:
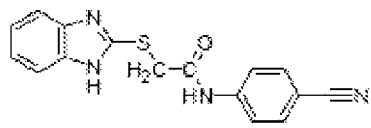
Figure 3A:
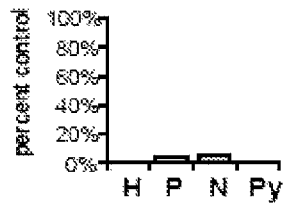
Figure 3A:
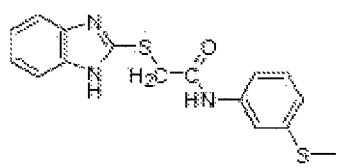
Figure 3A:
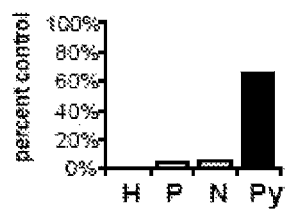
Figure 3A:
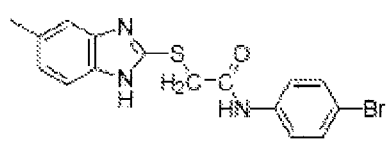
Figure 3A:
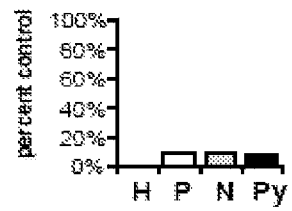
Figure 3A:
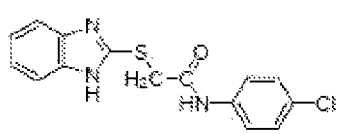
Figure 3A:
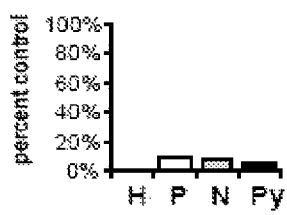
Figure 3A:
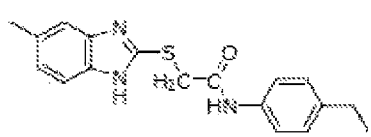
Figure 3A:
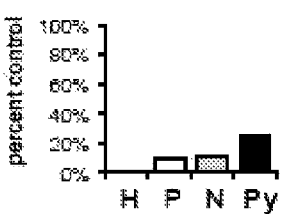
Figure 3A:
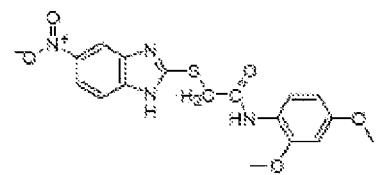
Figure 3A:
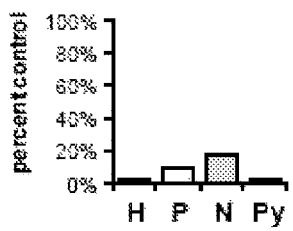
Figure 3B:
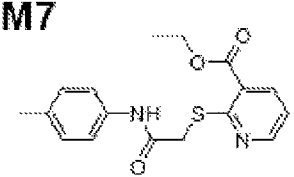
Figure 3B:
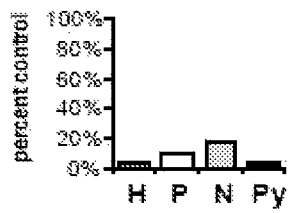
Figure 3B:
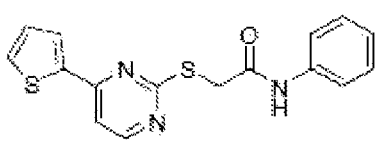
Figure 3B:
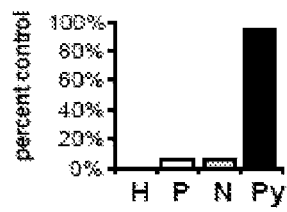
Figure 3B:
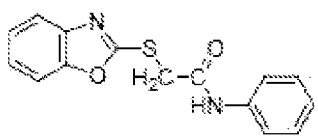
Figure 3B:
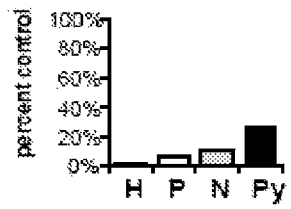
Figure 3B:
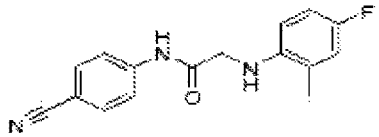
Figure 3B:
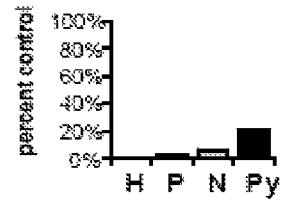
Figure 3B:
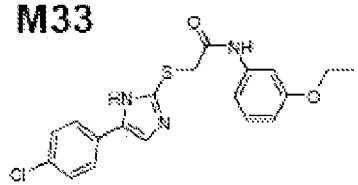
Figure 3B:
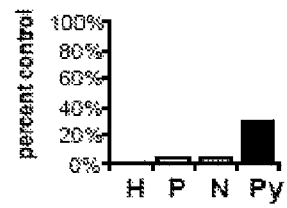
Figure 3B:
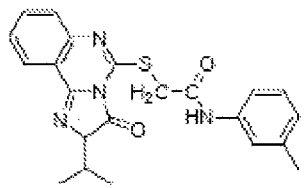
Figure 3B:
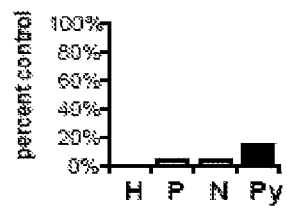
Figure 3C:
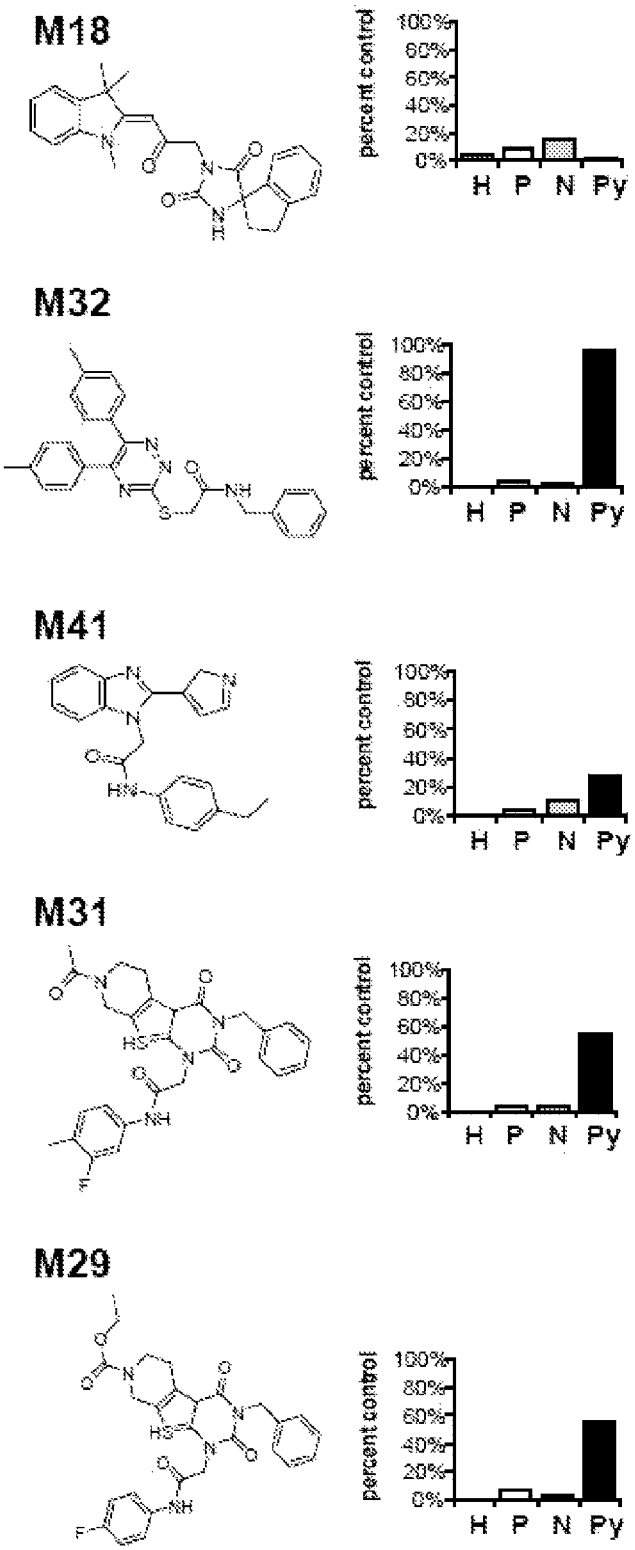

Compounds were tested at various concentrations for their impact on 4-hydroxy-2-alkylquinoline (HAQ) levels, including the MvfR ligands 4-hydroxy-2-heptylquinoline (HHQ) and 3,4-dihydroxy-2-heptylquinoline (PQS), as well as 2-n-heptyl-4-hydroxyquinoline-N-oxide (HQNO) and 2,4-dihydroxyquinoline (DHQ) (FIGS. 2A-2C). Levels of the phenazine, pyocyanin, an MvfR-regulated virulence factor, were also determined. At 50 µg/ml, the concentration used in the original screen, seventeen compounds decreased HAQ levels to less than 15% of the control (FIG. 3).

Figure 4:
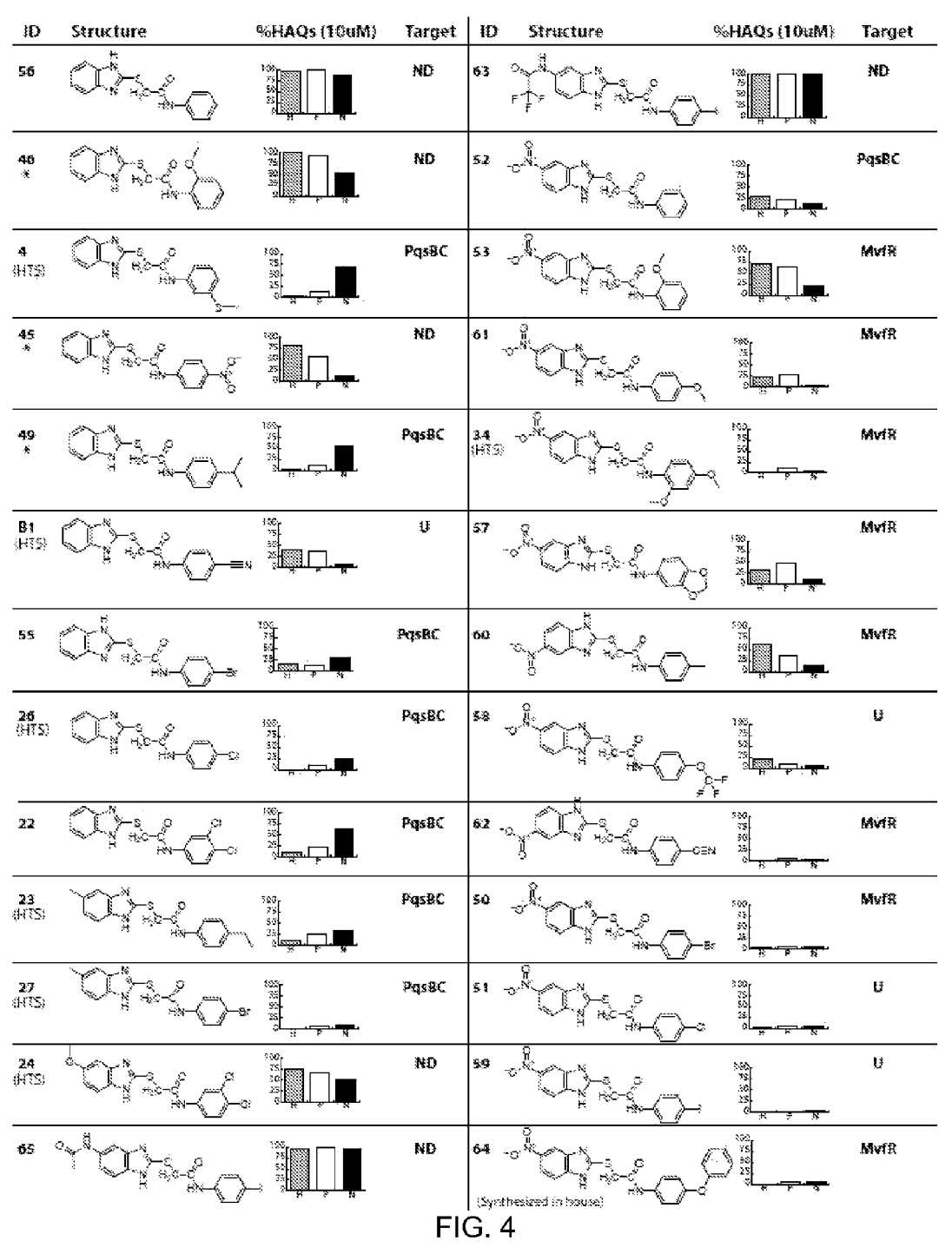

Six of these compounds were effective at concentrations as low as 10 µM (M34, M27, M29, M26, M31, and M4), a concentration 150 times lower than required for AA analogs previously identified. All compounds resulted in increased anthranilic acid (AA), likely since this molecule is not being utilized for HAQ production. Interestingly, some compounds inhibited HAQ production while not greatly impacting pyocyanin Twelve of the 17 compounds (B1, M7, M8, M17, M18, M19, M23, M26, M27, M33, M34, M41) also significantly restricted pyocyanin levels to less than half of the control (FIG. 4). The impact of various compounds on the acyl-homoserine lactone 3-oxo-C12-HSL and C4-HSL concentrations was also determined, though the levels of these molecules were similar to wild-type PA14.

Example 3

Structure-Activity Relationship

Benzamide-Benzimidazole Molecules are the Most Potent Mvfr Regulon Inhibitors

Several compounds (M4, M24, M23, M26, M27, M34, and B1), including the best inhibitors identified in the HTS, share a basic backbone of a benzamide-benzimidazole structure (FIGS. 3 and 4). Thus efforts were focused on commercially available variations of this backbone in an effort to understand what substitutions are critical for activity and to ultimately design more potent inhibitors. FIG. 4 compares various benzamide-benzimidazole structures assessed and their impacts on HAQ and pyocyanin levels when tested at 10 µM. Compound M56, which possesses the unsubstituted benzamide-benzimidazole structure, has little impact on pyocyanin or HAQ production. The presence of a methoxy group at the ortho position (M46) of the benzamide ring did not improve the activity, however a thiomethyl group at the meta position (M4) improved HAQ inhibition. A strong electron withdrawing group such as a nitro group in the para position of the benzamide ring (M45) did not improve the activity, but the isosteric isopropyl group at the same position (M49) did yield a more active compound. The presence of a cyano (B1), a bromo (M55) or a chloro (M26) substituent at the same para position produced active compounds. A second chlorine atom at the meta position on the benzamide ring, as in M22, decreased the activity as compared to M26. Substitution of the benzimidazole ring with a methyl group and of the benzamide ring with an ethyl group (M23) provided a moderately active compound as compared to M27 which shares the same methyl benzimidazole group but which contains a para-bromobenzamide function. Interestingly, M27 is more active than M55, which lacks the methyl group on the benzimidazole ring. A methoxy group instead of a methyl decreased the activity, when comparing M24 and M22. Attempts to substitute the benzimidazole ring with a trifluoroacetamide, as in M63, or with an acetamide group, as in M65, yielded inactive compounds compared to their nitro substituted counterpart M59.

The most active commercially available inhibitors generally all had a nitro substituted benzimidazole ring and a benzamide ring substituted at the para position with a methoxy (M61), trifluoromethoxy (M58), a cyano (M62), a bromo (M50), a chloro (M51) or a iodo (M59). The nitrobenzimidazole derived compound M53 with its benzamide group substituted with an ortho methoxy group was not very active while the ortho and para dimethoxy analogue M34 was quite active. In addition to the aforementioned commercially available molecules, 2-((6-nitro-1H-benzo[d]imidazol-2-yl)thio)-N-(4-phenoxyphenyl)acetamide (described above in Example 1) was synthesized, which has a nitro substituted benzimidazole ring and a para-phenoxy substituted benzamide ring (the compound is also referred to herein as M64). This compound proved to be one of the most effective at reducing both HAQ and pyocyanin at very low concentrations. Overall the most active inhibitors were found to be M64, M59 and M50, which considerably inhibited HAQs and pyocyanin in the nanomolar range.

Disrupting virulence factor production without impacting cell viability can provide an alternative to traditional antibiotics which promote the emergence of resistant microbes. MvfR-controlled QS system of *P. aeruginosa* was targeted as mutations in MvfR or the pqs operon do not impact bacterial cell growth. HTS yielded several novel MvfR pathway inhibitors that were not toxic to mammalian cells and were effective at micromolar concentrations. Analysis of the structure of these compounds showed that specifically substituted benzamide-benzimidazole molecules were potent MvfR regulon inhibitors, and by testing various modifications of this structure, potency was improved. These molecules effectively reduced HAQs and pyocyanin production at nanomolar concentrations, far exceeding the potency of previously reported inhibitors.

A variety of active structures was identified in the HTS, with only the substituted benzamide-benzimidazole core structure appearing in multiple hits. Several compounds, particularly M21 and M32, were effective HAQ inhibitors while not impacting pyocyanin levels at all. The regulation of pyocyanin production was complex and under the control of various environmental and genetic factors, so the explanation for this phenomenon remains unclear.

Example 4

Elucidating the Mechanism of Inhibition

Figure 5:
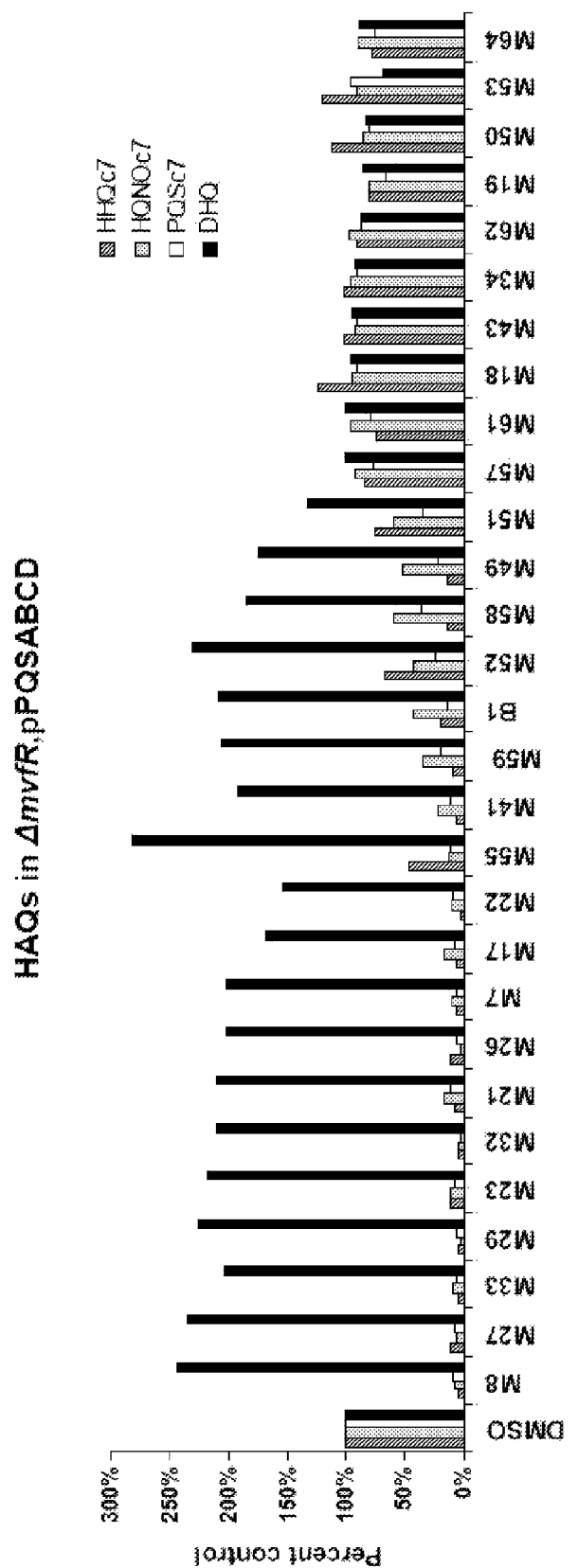
FIG. 5 is a bar graph depicting HAQ's levels in the presence of compounds from the high throughput screen.

The structures of the identified potent inhibitors did not resemble precursors or intermediates in the HAQ synthesis pathway, thus their mechanism of inhibition is unclear. However, since these compounds diminish or abolish *P. aeruginosa* HAQ production, it is possible that they target either the MvfR protein itself or enzymes in the pqs operon that are required for HAQ synthesis. To further understand the target (s) of these compounds, a ΔmvfR mutant constitutively expressing the pqsABCD genes was used. This strain is capable of synthesizing HHQ, HQNO, PQS and DHQ independently of MvfR. Using LC/MS, the production of HAQs was measured in the presence of 100 μM of selected inhibitors; many of them do not significantly alter HAQ levels compared to the solvent control (M18, M19, M34, M43, M50, M53, M57, M60, M61, and M62), suggesting that these compounds target MvfR or other components upstream of MvfR (FIG. 5). As shown in FIG. 5, another group of inhibitors reduced HHQ and HQNO levels but increased DHQ when present in this strain (M26, M27, M23, M4, M55, and M52). Since PqsA and PqsD are necessary and sufficient for DHQ production, it is possible that these inhibitors target either PqsB or PqsC enzymes, which are required for HHQ and PQS production. Finally, several inhibitors exhibited an intermediate phenotype in between those that inhibit MvfR and those inhibiting PqsB or PqsC (B1, M51, M59, and M58), implying that they may have dual or alternative targets.

Some compounds target MvfR directly, while others seem to target enzymes of the pqs operon, likely PqsB or PqsC, therefore these inhibitors worked via a novel mechanism. Those compounds that likely inhibited PqsB or PqsC also limited 4-hydroxy-3-methyl-2-alkylquinolines (HMAQs) in *Burkholderia thailandensis*, which had homologs of these genes; while compounds targeting MvfR had no impact in this species, likely since there was no *B. thailandensis* MvfR counterpart.

The nature of MvfR inhibition was unclear, but the compounds did not appear to render the protein less stable. It is possible that these molecules compete for PQS or HHQ ligand binding, though experiments to address this issue have been inconclusive. Structural information about the MvfR protein would be useful to identify a potential binding pocket for the compounds. Interestingly, all MvfR-specific inhibitors sharing the benzamide-benzimidazole basic structure contain a nitro group, and incidentally these molecules are the most effective in eliminating virulence in the yeast model. However, the nitro substitution on the benzamide-benzimidazole ring alone is not enough to confer MvfR-target specificity, as several molecules with this basic structure are clearly not targeting MvfR directly.

Example 5

Inhibitors are not Cytotoxic and can Effectively Attenuate Death in PA14-Exposed Macrophage Cell Lines Cell Culture Assays Raw264.7 macrophage cells were cultured in Dulbecco's modified eagles medium (DMEM) containing 10% FCS, 2 mM glutamine and antibiotic-antimycotic solutions. Before infections cells were washed with PBS (without Mg2+ and Ca2+) and antibiotic-free medium was used for infections. The cells were infected with PA14 and PA14 isolates grown in the presence of compounds at an MOI of 100 for 3 h at 37° C. in a 5% CO2 atmosphere. During infections cells were incubated with 100 μM of compounds as well. After 3 hours of PA14 infection, the cells were washed and incubated with DMEM medium containing polymixin B and gentamicin in order to kill the extracellular bacteria. The viability of Raw264.7 was assessed using the MTT assay, which detects the early sign of eukaryotic cell death. The formazan crystals formed in viable, metabolically active cells were dissolved by the addition of 100 µl DMSO and optical density was measured at 570 nm in a microplate reader.

Figure 6A:
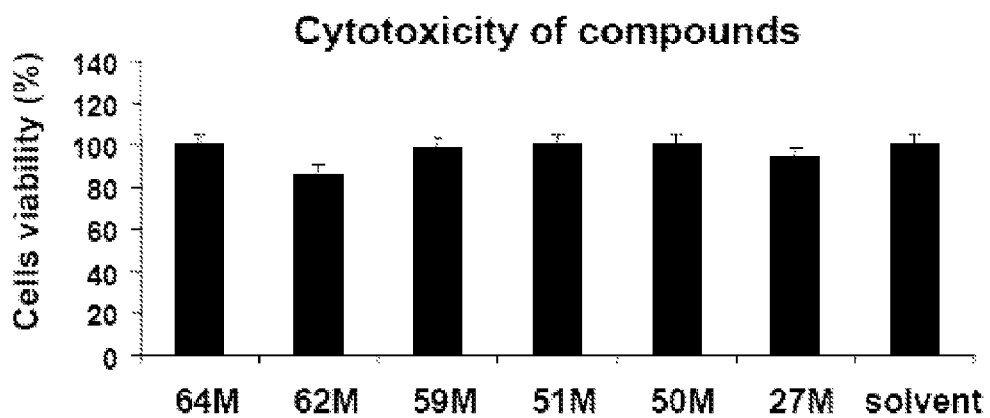
FIG. 6A is a bar graph depicting the cytotoxicity of the compounds M64, M62, M59, M51, M50, and M27.
Figure 6B:
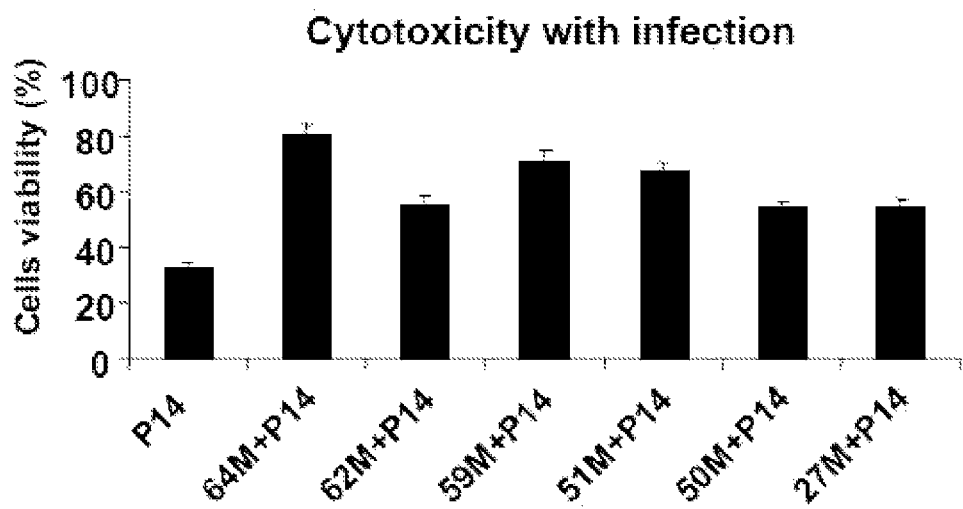
FIG. 6B is a bar graph depicting the cytotoxicity of infected cells in the presence of the compounds M64, M62, M59, M51, M50, and M27.

In order to determine whether or not the potent inhibitors are cytotoxic in eukaryotes, Raw 264.7 macrophage cells were exposed to selected compounds. No significant cytotoxicity was observed following compound exposure for 3 hours compared to the DMSO solvent control (FIG. 6A). The cytotoxicity of the macrophage cells was also determined when infected with PA14 bacterial cells alone or in the presence of the compounds. Incubation with PA14 cells resulted in only 33% viable macrophages, whereas addition of the anti-infective compounds significantly reduced cytoxicity (FIG. 6B). M64 resulted in the greatest improvement of viability with 80% of cells surviving post-infection. Both compounds that target PqsB/C (M27) or MvfR (M64, M50, M62) effectively reduced cytotoxicity in this system. These results suggest that the identified MvfR inhibitors can effectively reduce *P. aeruginosa* pathogenesis in vivo.

The most potent compounds were not cytotoxic to eukaryotic cells in the conditions tested, making them plausible anti-virulence factor pro-drugs. Furthermore, these compounds can significantly decrease cytotoxicity in macrophage cells infected with PA14 bacterial cells, and they eliminate killing in yeast incubated with PA14. The molecules identified in this study can provide the framework for the design of effective anti-virulence therapeutics at a time when new antimicrobials are in great demand.

Example 6

MvfR-Inhibitors Eliminate Killing in a Yeast-*Pseudomonas* Pathogenesis Assay

Yeast Virulence Assays

The *Cryptococcus neoformans* KN99 α, yeast strain was used to initially assess the impact of the compounds on virulence. Yeasts were mixed with YPD top agar and poured onto YPD plates. 1 µl of compound or DMSO solvent control was spotted onto the plate and allowed to dry. *P. aeruginosa* PA14 or control mvfR mutant cells were inoculated as 1 µl spotted directly on top of the dried solvent or compound. The impact of compound on virulence was assessed by comparing the clearing zone around the bacteria to PA14+ solvent (large zone, control for killing) or the mvfR mutant+solvent (no killing zone).

Figure 7:
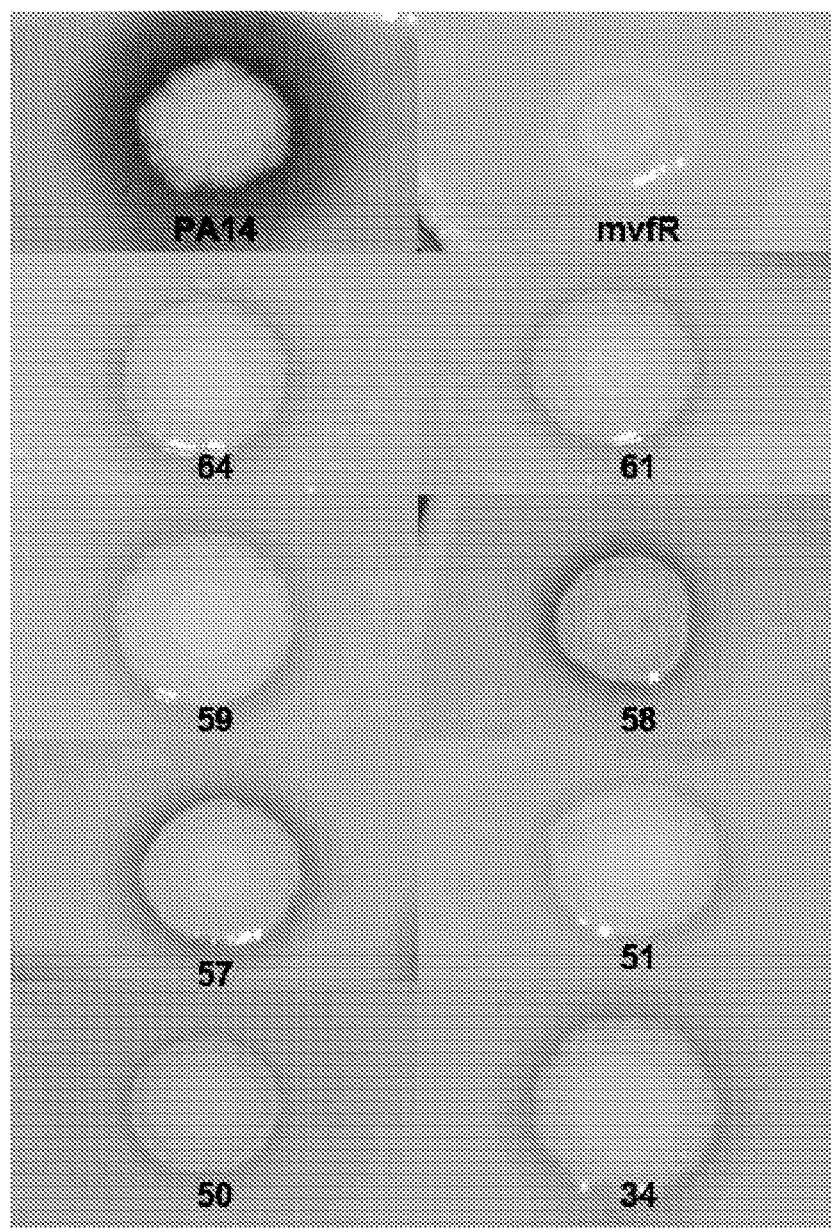
FIG. 7 are images of yeast plated in a yeast killing assay in the presence of the compounds M34, M50, M51, M57, M58, M59, M61, and M64.

A yeast killing assay was used to initially determine the in vivo impact of the most potent compounds on pathogenesis. In this system, a ΔmvfR mutant was completely avirulent compared to PA14, thus allowing for a clear comparison with MvfR inhibitors. *Cryptococcus neoformans* was used as the model yeast and plated as a top agar suspension. 1 µl of a 10 mM DMSO solution of the inhibitors or DMSO control was spotted onto the plate followed by a 1 µl inoculation of either PA14 or ΔmvfR cells in the same location. Compounds were also spotted alone to determine toxicity to the yeast. After 2-3 days of growth, the zone of inhibition surrounding the bacteria and compound inoculum was compared to PA14 with DMSO (zone of clearing) and ΔmvfR with DMSO (no clearing zone). Several compounds, including M34, M50, M51, M59, and M61 eliminated bacterially-induced yeast killing, while M58 and M57 had reduced clearing zones (FIG. 7). Several potent HAQ inhibitors, including M26, M27, M52, M53, and M55 were not effective at reducing virulence in the yeast model. Interestingly, all compounds effectively eliminating virulence contained a nitro group, suggesting that this substitution is critical for in vivo activity, however not all nitro-containing compounds were effective, indicating that substitution on the benzamide ring was also important for attenuating virulence.

Example 7

MvfR Inhibitors Attenuate Virulence in a Murine Burn and Infection Model

Mouse Burn and Infection Model.

A thermal injury mouse model was used as described previously to assess bacterial pathogenicity in 6 week old BALBC mice (Charles River Laboratories). Following mouse anesthetization, a full-thickness thermal burn injury involving 5%-8% of the body surface area was produced on the dermis of the shaved abdomen. An inoculum of $4 \times 10^4$ PA14 cells, corresponding to a lethal dose of 50%, was injected intradermally into the burn eschar along with the compound or solvent, prepared as follows: 5 µl of a 50 mM stock in DMSO of compound was added to a solution of 5% CremophorEL/Ethanol (50/50% vol) in 50 µl saline. Assuming each mouse has approximately 2.5 ml of blood, this injection corresponds to ~100 µM inhibitor/mouse/injection. Each mouse also received IV injections of 50 µl of compound or solvent, as prepared above at 6 hours and 24 hours post-infection.

Figure 8:
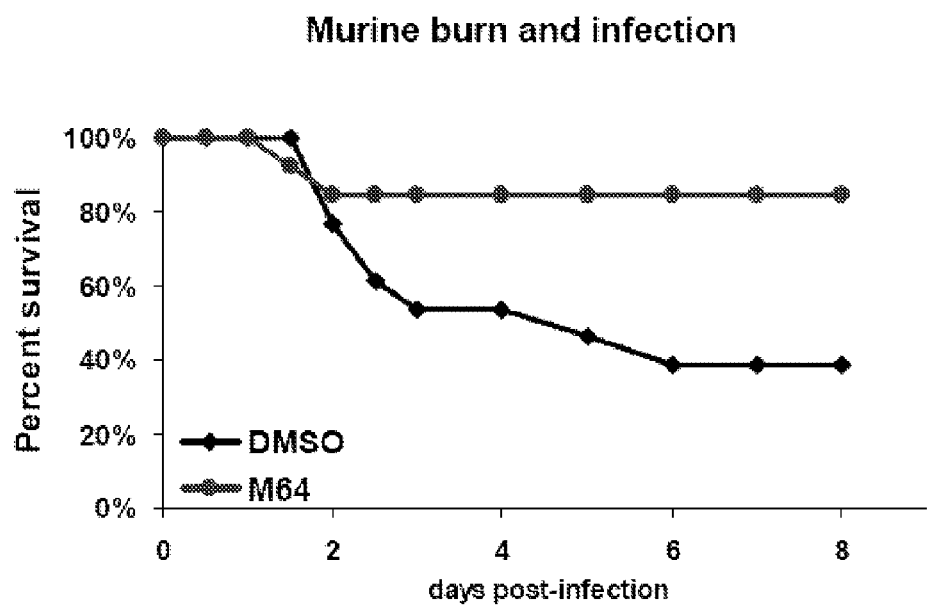
FIG. 8 is a graph depicting percent survival of a thermal injury mouse model.

A murine thermal injury and infection model was used to assess the impact of the compounds on *P. aeruginosa* pathogenesis in animals. Due to the hydrophobic nature of the compounds, 5% CremophorEL/Ethanol (50/50% vol) was used as an emulsifier to dissolve the compound in saline prior to injecting into animals. The bacterial cultures were grown in the presence of 10 µM of the inhibitor. The bacteria and either 100 µM compound/mouse or DMSO control were co-injected at the time of infection. Compounds were also injected 6 hours and 24 hours post-infection. M64 resulted in 84% overall surviving mice compared to the solvent control, for which only 38% survived (FIG. 8). These results indicated that this compound has an important anti-virulence effect in vivo, and supports the notion that MvfR inhibitors could be developed into novel anti-infective therapeutics.

Example 8

MvfR Inhibitor M64 Plus Ciprofloxacin Attenuates Virulence in a Murine Burn and Infection Model A murine thermal injury model (Stevens et al., J Burn Care Rehabil. 1994; 15:232-235) was used as previously described to further assess bacterial pathogenicity in 6-wk-old DC-1 mice (Rahme et al., Science, 268(5219): p. 1899-902 (1995)) in the presence of combination of Ciprofloxacin (Bayer AG) and M64. Following mouse anesthetization, a full-thickness thermal burn injury involving 5%-8% of the body surface area was produced on the dermis of the shaved abdomen, and an inoculum of about $6-7 \times 10^3$ PA14 cells was injected intradermally into the burn eschar along with DMSO or 100 µM M64 compound. 100 µM (4 mg/Kg) of M64, 0.4 mg/Kg of ciprofloxacin (lower than the recommended dose of 10 mg/Kg), or a combination of M64+ciproflocaxin was also injected IV via tail vein at 6, 20, 28, 40, 60, 68 h and 80 h post-infection. Mice survival was subsequently assessed over the course of 7 days. Ten animals per treatment were used. In this set of experiments the concentration of ciprofloxacin used was lower than the therapeutic levels recommended to permit assessment of the possible synergistic effect between M64 and ciprofloxacin. The recommended dose of 10 mg/Kg ciprofloxacin is expected to clear infection.

Figure 9A:
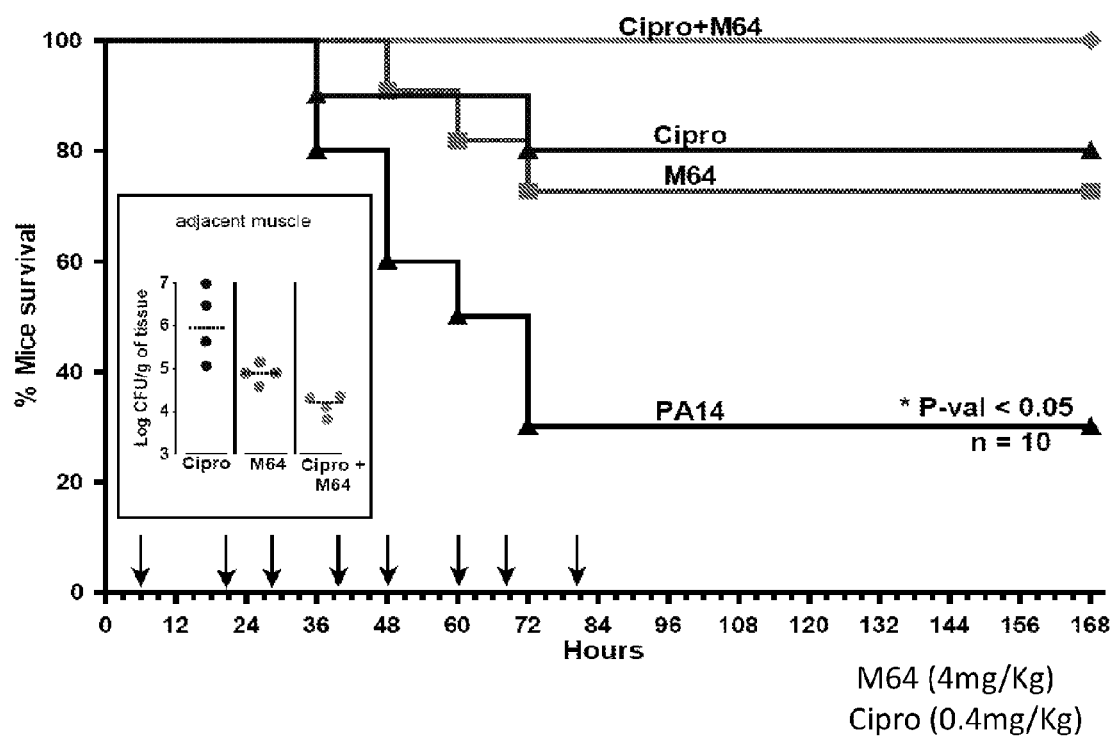
FIG. 9A is a line graph showing percent survival in a murine burn and infection model after administration of M64 plus Ciprofloxacin.
Figure 9B:
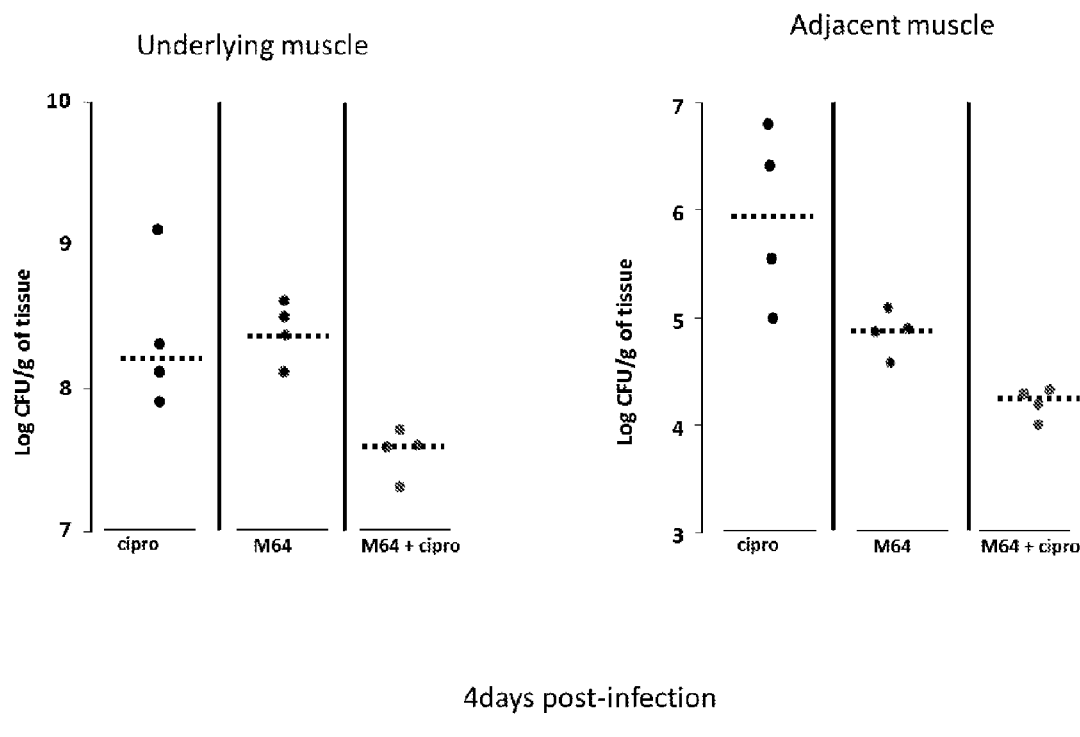
FIG. 9B is a pair of line graphs showing bacterial loads were lower in M64+ciprofloxacin mice in muscle samples taken adjacent to burn wound (adjacent muscle, right graph) than in mice treated with M64 or ciprofloxacin alone.

FIG. 9A shows that M64 and Ciprofloxacin limited *P. aeruginosa* virulence in vivo, wherein mice were administered multiple intravenous injections of M64 or ciprofloxacin alone or in combination at 6, 20, 28, 40, 60, 68 h and 80 h after injury and infection. While the un-injected controls exhibited 30% survival to *P. aeruginosa* infection, mice injected with M64, ciprofloxacin or the combination of thereof, exhibited significant increased survival rates, 75%, 80% or 100% respectively. The combination M64+ ciprofloxacin promoted 100% survival. Furthermore, M64+ ciprofloxacin synergized in restricting bacterial dissemination in mice better than M64 or ciprofloxacin alone. FIG. 9B shows that bacterial loads are lower in M64+ ciprofloxacin mice in muscle samples taken adjacent to burn wound (adjacent muscle) than in mice treated with M64 or ciprofloxacin alone.

These results indicate that the anti-virulence effect of M64 can increase survival rate of infected animals even when low concentrations of antibiotic are used in combination.

Example 9

Chromatin Immunoprecipitation (ChIP) Studies

Figure 10:
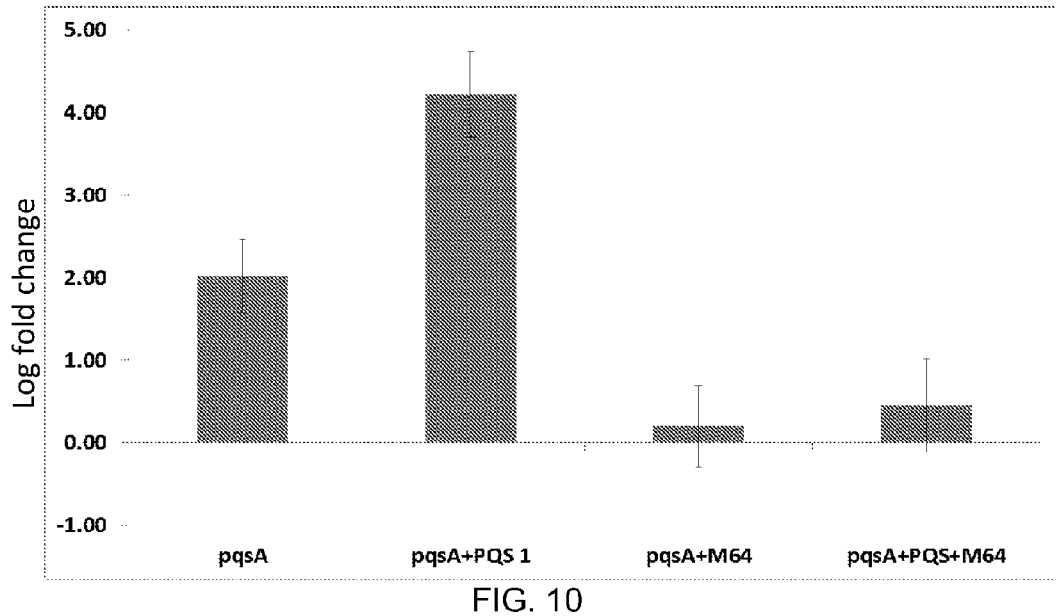
FIG. 10 is a bar graph showing that M64 interferes with MvfR binding to pqsA promoter by competing with MvfR ligands.

To probe the mode of action of M64 and determine the inhibitors' involvement in MvfR binding to the pqs and phnAB operon promoter. MvfR was fused to a vesicular stomatitis virus glycoprotein (VSV-G) epitope tag (Castang et al., Proc Natl Acad Sci USA. 2008; 105(48):18947-52) and introduced into PA14 cells. As a negative control, the ability of the tagged MvfR protein to bind non-MvfR regulated gene promoters (i.e. rpoD) was tested. ChIP studies were performed in the presence and absence of M64 inhibitors and in the absence and presence of exogenously added ligand PQS using the VSV-G-tagged MvfR in PA14 cells. LB broth aliquots (5 ml) were inoculated (at $OD_{600}$≈0.03) and grown at 37° C. to an $OD_{600}$ of 1.5-2.5, in the presence or absence of each inhibitor (10 and 100 mM). Cross-linking and ChiP were performed as described previously (Castang et al., Proc Natl Acad Sci USA. 2008; 105(48):18947-52). Quantitative PCR was performed using oligonucleotides corresponding to known MvfR binding sites in the pqs operon region (Cao et al., Proc Natl Acad Sci USA. 2001; 98(25):14613-8, Xiao et al., Microbiology. 2006; 152(Pt 6):1679-86). Using iTaq SYBR green with ROX (Bio-RAD) and an Applied Biosystems StepOne-Plus detection system, ChiP fold enrichment values were calculated (Castang et al., Proc Natl Acad Sci USA. 2008; 105(48):18947-52). These values represent the relative abundance of a sequence of interest versus a negative control region and in absence of inhibitors. All ChiP fold enrichment values represent the average of at least three biological replicates. The results, shown in FIG. 10, suggest that M64 affects MvfR binding to pqsA promoter by competing with the MvfR ligand PQS. It is likely that the same occurs with the other MvfR ligand HHQ.

Example 10

Polymicrobial Infections and Tolerance in *Klebsiella* and *Acinetobacter*

Human chronic wound infections involving *Pseudomonas aeruginosa* are typically polymicrobial, which impair healing and clearance compared to monomicrobial infections (Dalton et al., PLoS One, 2011. 6(11): p. e27317). Moreover, bacteria isolated from polymicrobial wound infections display increased antimicrobial tolerance in comparison to those in single species infections (Dalton et al., PLoS One, 2011. 6(11): p. e27317). This suggests possible synergistic interactions among bacteria in polymicrobial communities.

To investigate this, 2-AA was added to exponentially growing cultures of *A. baumaniii* and *Klebsiella pneumonia*. 2-AA is a volatile, low molecular weight molecule, 2-amino acetophenone (2-AA), produced by the opportunistic human pathogen *Pseudomonas aeruginosa* that reduces bacterial virulence in vivo in flies and in an acute mouse infection model (Kesarwani et al., PLoS Pathog. 2011 August; 7(8): e1002192. Epub 2011 Aug. 4). The results, shown in FIG. 11, show that exogenous 2-AA increases the antibiotic tolerant cell fraction.

Figure 11:
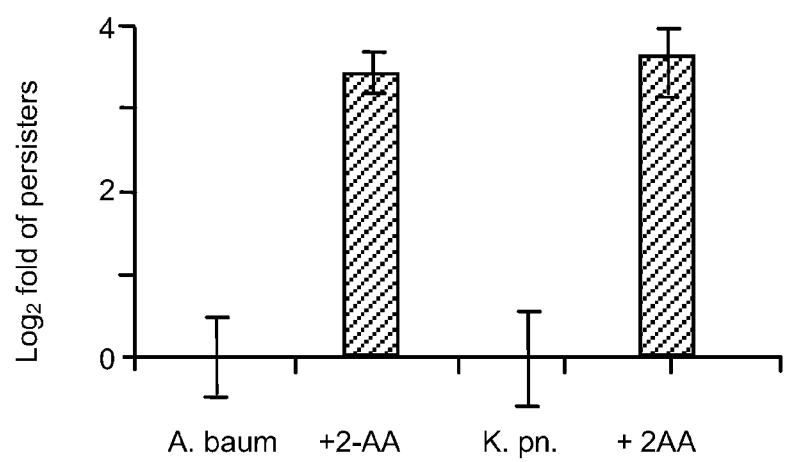
FIG. 11 is a bar graph showing that Exogenously addition of 2-AA to exponentially growing cultures of *A. baumannii* (*A. baum*) or *Klebsiella pneumoniae* (*K. pn.*) (green) increases the antibiotic tolerant cell fraction.

These results suggest that 2-aminoacetophenon, an excreted small molecule whose synthesis is regulated by MvfR and the enzymes encoded by the pqs operon genes may promote antibiotic tolerance in polymicrobial settings (e.g., wounds, lungs) in both *K. pneumoniae* and *A. baumannii* (FIG. 11). These two bacterial pathogens are frequently isolated from polymicrobial infections, together with *P. aeruginosa* (Rezaie et al., Burns, 2011. 37(5): p. 805-7). Since exogenous addition of 2-AA enriches the accumulation of antibiotic tolerant cells in these pathogens, and since the inhibitors described herein target MvfR and inhibit the synthesis of the molecules synthesized by the pqs operon, it is expected that the inhibitors described herein, including M64, decrease antibiotic tolerance also in these organisms.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A compound of Formula I:

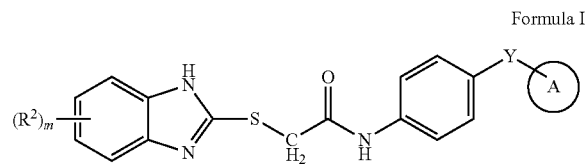

Formula I or a pharmaceutically acceptable salt thereof, wherein:
Y is O;
Ring A is aryl, heteroaryl, or heterocycloalkyl, wherein ring A is unsubstituted or substituted by 1 to 5 $R^1$;
$R^1$ is —$NR^aR^b$, $NO_2$, or —$NHC(O)R^c$; or two $R^1$ together with the carbon atoms to which they are attached form a heteroaryl or heterocycloalkyl;
$R^2$ is —$NR^aR^b$, —$NHC(O)R^a$, $NO_2$, —CN, —$SR^a$, or —$S(O)_2R^a$;
$R^a$ and $R^b$ are each independently H or $C_{1-6}$ alkyl;
$R^c$ is H, $C_{1-6}$ alkyl, or $C_{1-6}$ haloalkyl; and
m is 1, 2, 3, or 4.
2. The compound of claim 1, or a pharmaceutically acceptable salt thereof,
wherein Y is O and Ring A is phenyl substituted by 1 to 5 $R^1$.

3. A compound which is:

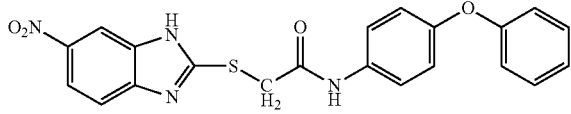 [SMILES: O=C(CSc1nc2ccc([N+](=O)[O-])cc2[nH]1)Nc1ccc(Oc2ccccc2)cc1]

2-((6-nitro-1H-benzo[d]imidazol-2-yl)thio)-N-(4-phenoxyphenyl)acetamide, or a pharmaceutically acceptable salt thereof.

4. A pharmaceutically acceptable composition comprising a compound of Formula I:

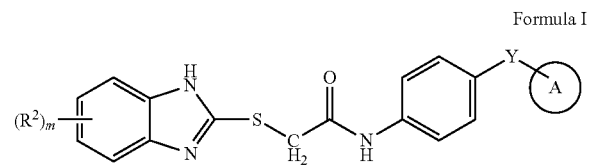

Formula I or a pharmaceutically acceptable salt thereof, wherein:
Y is O;
Ring A is aryl, heteroaryl, or heterocycloalkyl, wherein ring A is unsubstituted or substituted by 1 to 5 $R^1$;
$R^1$ is $C_1$-$C_6$ alkyl, —$NR^aR^b$, $NO_2$, or —$NHC(O)R^c$; or two $R^1$ together with the carbon atoms to which they are attached form a heteroaryl or heterocycloalkyl;
$R^2$ is —$NR^aR^b$, —$NHC(O)R^a$, $NO_2$, —CN, —$SR^a$, or —$S(O)_2R^a$;
$R^a$ and $R^b$ are each independently H or $C_{1-6}$ alkyl;
$R^c$ is H, $C_{1-6}$ alkyl, or $C_{1-6}$ haloalkyl; and
m is 1, 2, 3, or 4;
and
a pharmaceutically acceptable carrier.

5. The composition of claim 4, wherein Y is O and Ring A is phenyl substituted by 1 to 5 $R^1$.

6. The composition of claim 5, wherein the compound is

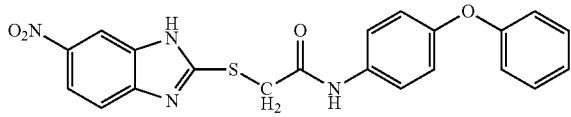 [SMILES: O=C(CSc1nc2ccc([N+](=O)[O-])cc2[nH]1)Nc1ccc(Oc2ccccc2)cc1]

2-((6-nitro-1H-benzo[d]imidazol-2-yl)thio)-N-(4-phenoxyphenyl)acetamide,
or a pharmaceutically acceptable salt thereof.

7. A method of treating an antibiotic-tolerant infection in a subject, the method comprising administering to the subject a therapeutically effective amount of a composition of claim 4.

8. The method of claim 7, wherein the compound is 2-((6-nitro-1H-benzo[d]imidazol-2-yl)thio)-N-(4-phenoxyphenyl)acetamide, or a pharmaceutically acceptable salt thereof.

9. The method of claim 7, wherein the bacterial infection or antibiotic-tolerant infection is caused by a Gram-negative bacterium.

10. The method of claim 9, wherein the gram-negative bacterium is selected from the group consisting of: *Pseudomonas aeruginosa* and *Burkholderia* species.

11. The method of claim 7, further comprising administering an antibiotic selected from the group consisting of: penicillins, cephalosporins, carbacephems, cephamycins, carbapenems, monobactams, quinolones, tetracyclines, aminoglycosides, macrolides, glycopeptides, chloramphenicols, glycylcyclines, licosamides, lipopeptides, oxazolidinones and fluoroquinolones.

12. The method of claim 7, wherein the bacterial infection is selected from the group consisting of: pneumonia, septic shock, urinary tract infection, a gastrointestinal infection, and an infection of the skin and soft tissue.

13. The method of claim 7, wherein the subject is a mammal or plant.

14. A method of treating a Gram negative infection in a subject, the method comprising administering to said subject in need of such treatment a composition of claim 4.

15. The method of claim 14, wherein the Gram negative infection is caused by *Pseudomonas aeruginosa*.

16. The method of claim 14, wherein the subject is a trauma patient or a burn patient suffering from a burn or skin wound.

17. A method of reducing bacterial tolerance in a subject, the method comprising administering to said subject a composition of claim 4.

18. The method of claim 14, further comprising identifying said subject as suffering from a bacteria tolerant infection.

19. The method of claim 14, further comprising co-administering to said subject an antibiotic.

20. The method of claim 19, wherein said antibiotic is a quinolone antibiotic.

* * * * *